US012678219B2

(12) United States Patent　　(10) Patent No.:　US 12,678,219 B2

Mixter et al.　　(45) Date of Patent:　Jul. 14, 2026

(54) MEDICAL TOOL POSITIONING DEVICES, SYSTEMS, AND METHODS OF USE AND MANUFACTURE

(71) Applicant: NuVera Medical, Inc., Los Gatos, CA (US)

(72) Inventors: Colin Mixter, Santa Clara, CA (US); Marc Bitoun, Santa Cruz, CA (US); Alan Schaer, San Jose, CA (US); Tom Saul, Moss Beach, CA (US)

(73) Assignee: NuVera Medical, Inc., Los Gatos, CA (US)

( * ) Notice: Subject to any disclaimer, the term of this patent is extended or adjusted under 35 U.S.C. 154(b) by 1008 days.

(21) Appl. No.: 17/602,362

(22) PCT Filed: Apr. 27, 2020

(86) PCT No.: PCT/US2020/030114

§ 371 (c)(1),
(2) Date: Oct. 8, 2021

(87) PCT Pub. No.: WO2020/220033

PCT Pub. Date: Oct. 29, 2020

(65) Prior Publication Data

US 2022/0168041 A1　　Jun. 2, 2022

Related U.S. Application Data

(60) Provisional application No. 62/839,520, filed on Apr. 26, 2019.

(51) Int. Cl.
A61B 18/14　　(2006.01)
A61B 8/00　　(2006.01)
(Continued)

(52) U.S. Cl.
CPC ............ *A61B 18/1492* (2013.01); *A61B 8/12* (2013.01); *A61B 8/445* (2013.01);
(Continued)

(58) Field of Classification Search
CPC ... A61B 18/1492; A61B 8/12; A61B 17/2202; A61B 2017/22021; A61B 2034/715;
(Continued)

(56) References Cited

U.S. PATENT DOCUMENTS 4,920,980 A  *  5/1990  Jackowski  ........... A61N 1/0565
604/95.04
5,441,483 A  8/1995  Avitall
(Continued)

FOREIGN PATENT DOCUMENTS

CN　　103442631 A　　12/2013
EP　　1849414 A1　　10/2007
(Continued)

OTHER PUBLICATIONS

Office Action received for Japanese Patent Application No. 2021-563291, mailed on Feb. 6, 2024, 6 pages (2 pages of English Translation and 4 pages of Original Document).
(Continued)

*Primary Examiner* — Joseph A Stoklosa
*Assistant Examiner* — Marina Delaney Templeton
(74) *Attorney, Agent, or Firm* — Smith, Gambrell & Russell LLP

(57)　　ABSTRACT

Steerable medical devices that include one or more elongate shafts and a medical tool in a distal region. The medical devices include a handle portion for controlling one or more aspects of the medical device.

19 Claims, 21 Drawing Sheets

(51) Int. Cl.
*A61B 8/12* (2006.01)
*A61M 25/01* (2006.01)

(52) U.S. Cl.
CPC .... *A61M 25/0136* (2013.01); *A61M 25/0147* (2013.01); *A61M 25/0133* (2013.01)

(58) Field of Classification Search
CPC . A61B 2562/222; A61B 8/445; A61B 8/4461; A61B 8/4466; A61B 17/22004; A61B 2017/00106; A61M 25/0147; A61M 25/0136; A61M 25/0133; A61M 2025/015
See application file for complete search history.

(56) References Cited

U.S. PATENT DOCUMENTS

| | | | |
|---|---|---|---|
| 6,100,626 A | 8/2000 | Frey | |
| 6,537,217 B1 | 3/2003 | Bjaerum et al. | |
| 6,559,389 B1 | 5/2003 | Kornrumpf et al. | |
| 7,257,051 B2 | 8/2007 | Thomenius | |
| 7,297,118 B2 | 11/2007 | Kristoffersen | |
| 7,331,927 B2 | 2/2008 | Steen | |
| 7,338,450 B2 | 3/2008 | Kristoffersen | |
| 7,451,650 B2 | 11/2008 | Halvorsrod | |
| 7,527,591 B2 | 5/2009 | Haugen | |
| 7,527,592 B2 | 5/2009 | Haugen | |
| 7,569,015 B2 | 8/2009 | Donaldson | |
| 7,621,028 B2 | 11/2009 | Gelly | |
| 7,731,516 B2 | 6/2010 | Puttinger | |
| 7,740,584 B2 | 6/2010 | Donaldson | |
| 7,762,954 B2 | 7/2010 | Nix et al. | |
| 7,766,833 B2 | 8/2010 | Lee | |
| 7,783,339 B2 | 8/2010 | Lee | |
| 7,791,252 B2 | 9/2010 | Baumgartner | |
| 7,819,802 B2 | 10/2010 | Secora | |
| 7,824,335 B2 | 11/2010 | Wodnicki | |
| 7,966,058 B2 | 6/2011 | Xue | |
| 8,057,397 B2 | 11/2011 | Li | |
| 8,096,951 B2 | 1/2012 | Kristoffersen | |
| 8,207,652 B2 | 6/2012 | Baumgartner | |
| 8,213,693 B1 | 7/2012 | Li | |
| 8,364,242 B2 | 1/2013 | Li | |
| 8,428,690 B2 | 4/2013 | Li | |
| 8,451,155 B2 | 5/2013 | Amemiya | |
| 8,527,032 B2 | 9/2013 | Li | |
| 8,659,212 B2 | 2/2014 | Eggen | |
| 8,721,553 B2 | 5/2014 | Lee | |
| 8,727,993 B2 | 5/2014 | Lee | |
| 8,742,646 B2 | 6/2014 | Wodnicki | |
| 8,776,335 B2 | 7/2014 | Baumgartner | |
| 8,790,262 B2 | 7/2014 | Li | |
| 8,933,613 B2 | 1/2015 | Amemiya | |
| 8,978,216 B2 | 3/2015 | Calisti | |
| 8,989,842 B2 | 3/2015 | Li | |
| 9,055,883 B2 | 6/2015 | Tgavalekos | |
| 9,439,625 B2 | 9/2016 | Cogan | |
| 9,575,165 B2 | 2/2017 | Miller | |
| 9,639,056 B2 | 5/2017 | Falter | |
| 10,070,793 B2 | 9/2018 | Flaherty et al. | |
| 2004/0102701 A1 | 5/2004 | Nix et al. | |
| 2008/0119738 A1 | 5/2008 | Imahashi et al. | |
| 2008/0287783 A1 | 11/2008 | Anderson | |
| 2012/0283570 A1 | 11/2012 | Tegg | |
| 2015/0359509 A1* | 12/2015 | Kim | A61B 8/445 600/467 |
| 2018/0098821 A1* | 4/2018 | Saul | A61B 8/12 |
| 2018/0279994 A1 | 10/2018 | Schaer | |

FOREIGN PATENT DOCUMENTS

| | | | |
|---|---|---|---|
| JP | 10-225457 A | 8/1998 | |
| JP | 2004-504093 A | 2/2004 | |
| JP | 2006-212353 A | 8/2006 | |
| JP | 2007-037786 A | 2/2007 | |
| JP | 2015-523868 A | 8/2015 | |
| WO | WO 2001/036017 | 5/2001 | |
| WO | 2013/154684 A1 | 10/2013 | |
| WO | WO 2018/017717 | 1/2018 | |
| WO | WO 2018/182836 | 10/2018 | |
| WO | PCT/US2019/061228 | 11/2019 | |

OTHER PUBLICATIONS

International Search Report mailed Jul. 30, 2020 from corresponding PCT Patent Application No. PCT/US2020/30114.
U.S. Appl. No. 62/760,784, filed Nov. 13, 2018.
Supplementary European search report and Search Opinion Received for EP Application No. 20795763.0, mailed on Dec. 23, 2022, 8 pages.

* cited by examiner

SECTION A-A

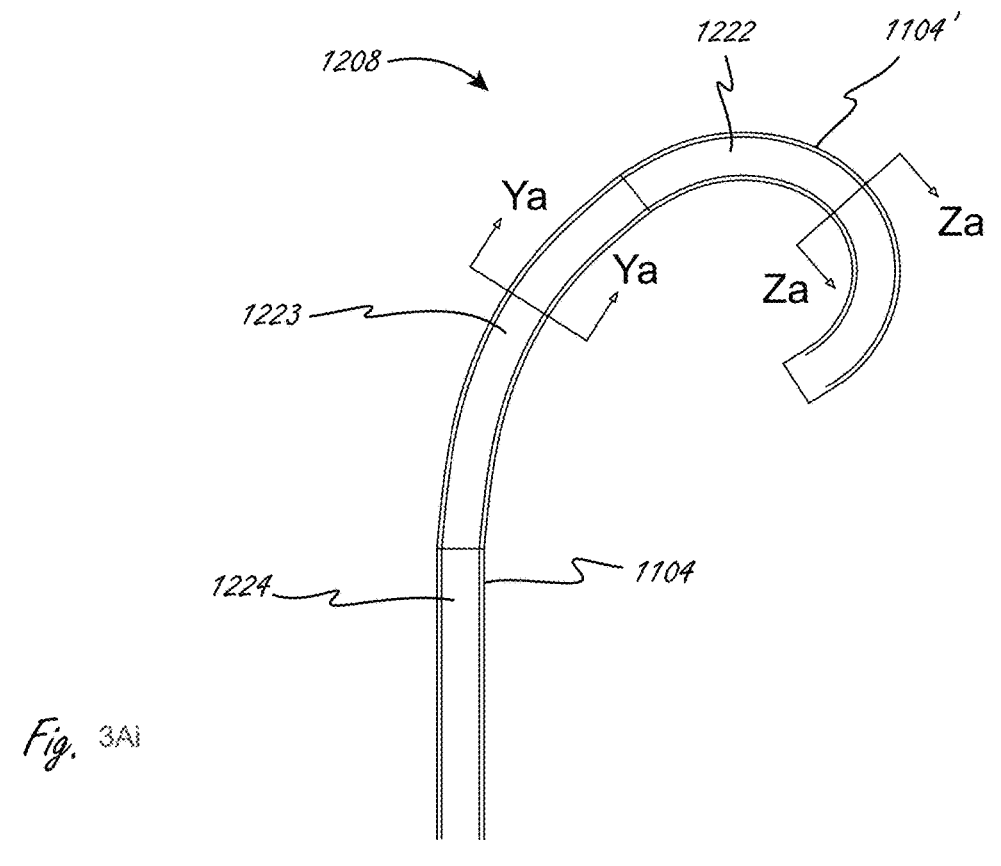
*Fig.* 3Ai
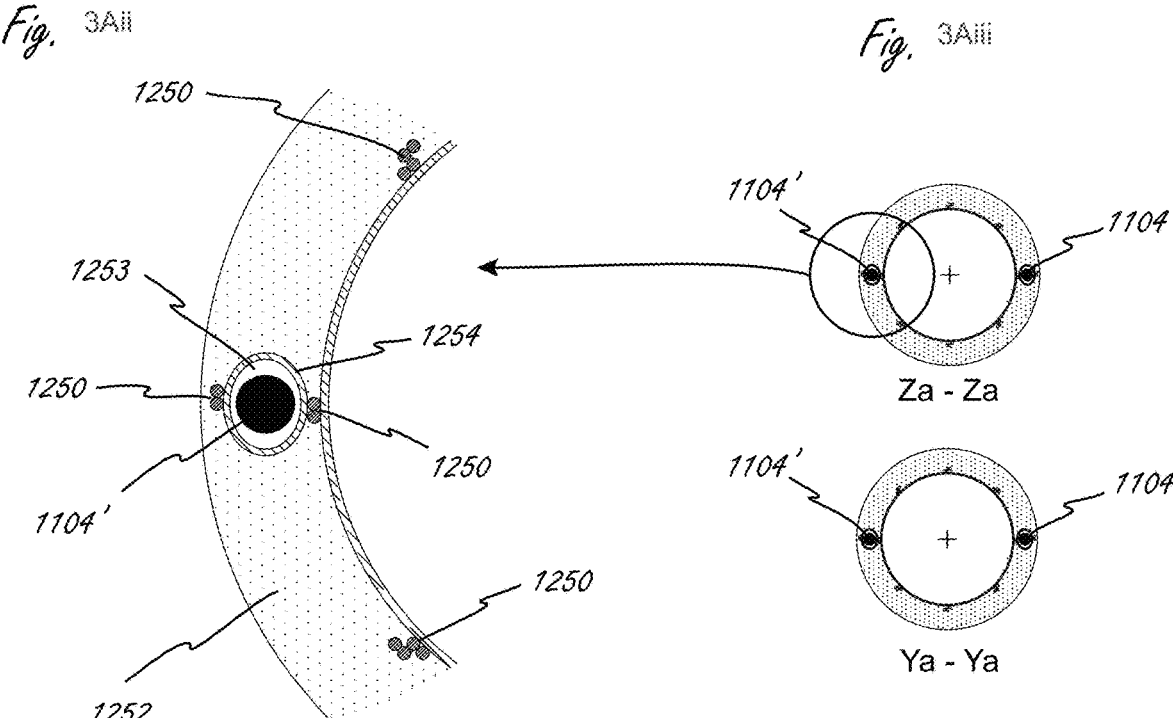
*Fig.* 3Aii
*Fig.* 3Aiii
Za - Za
Ya - Ya

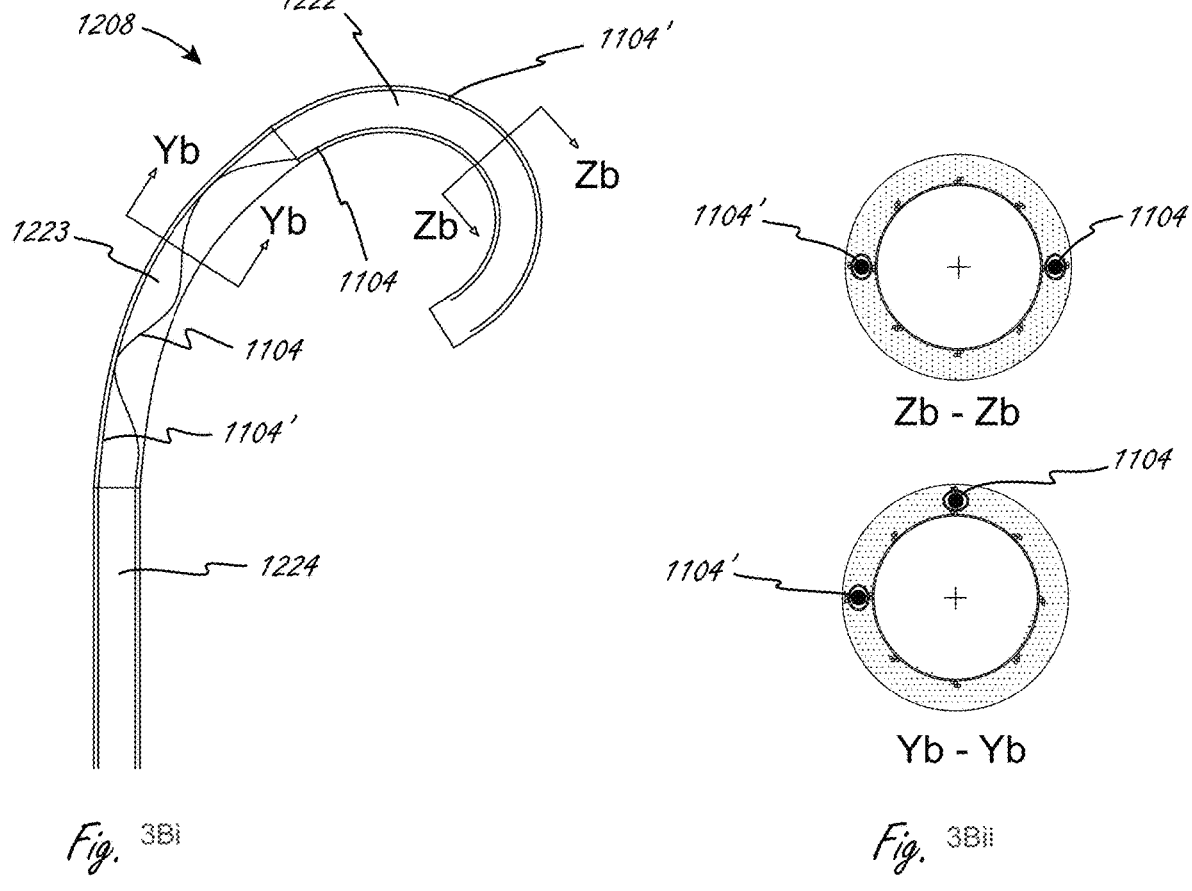
*Fig.* 3Bi
*Fig.* 3Bii

Fig. 3Cii

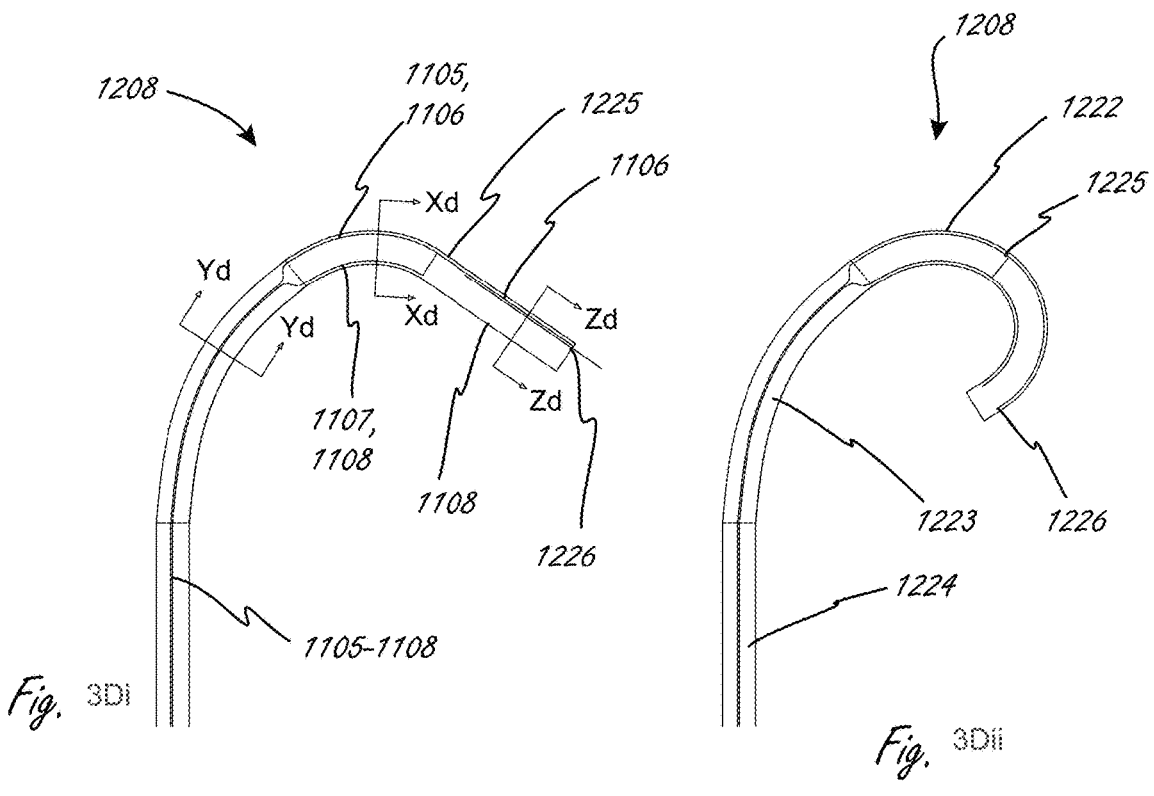
*Fig.* 3Di
*Fig.* 3Dii
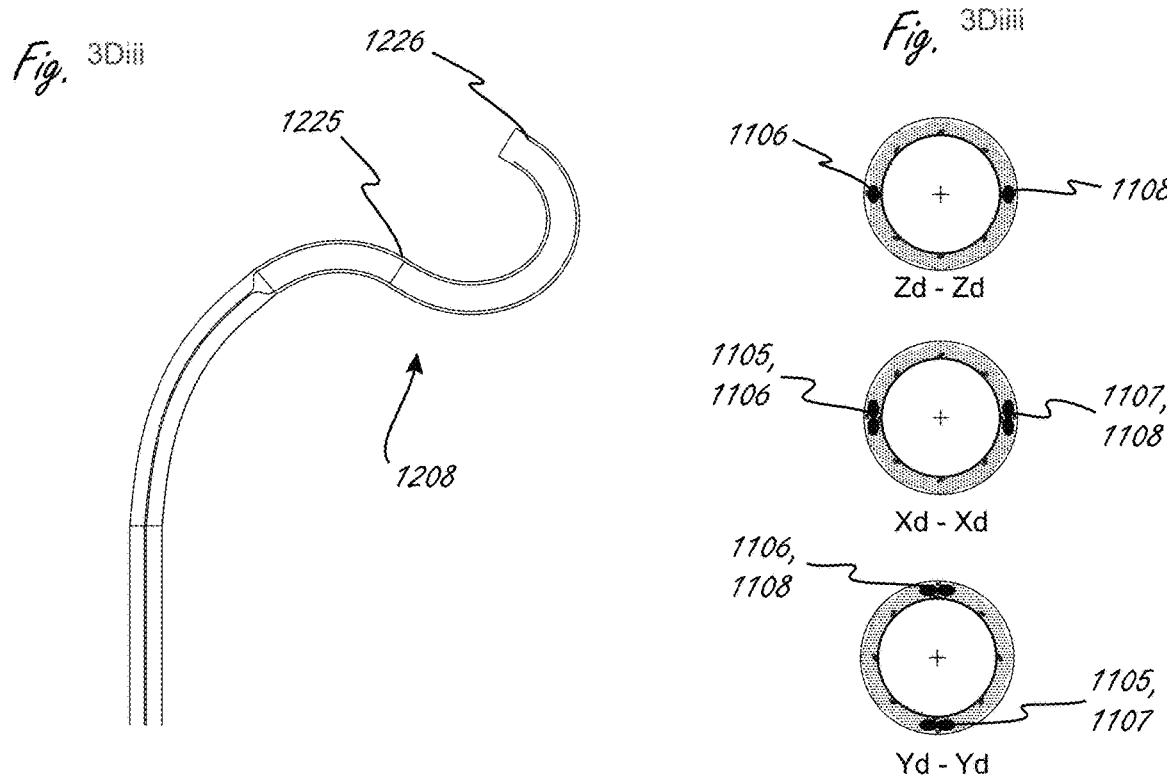
*Fig.* 3Diii
*Fig.* 3Diiii
Zd - Zd
Xd - Xd
Yd - Yd

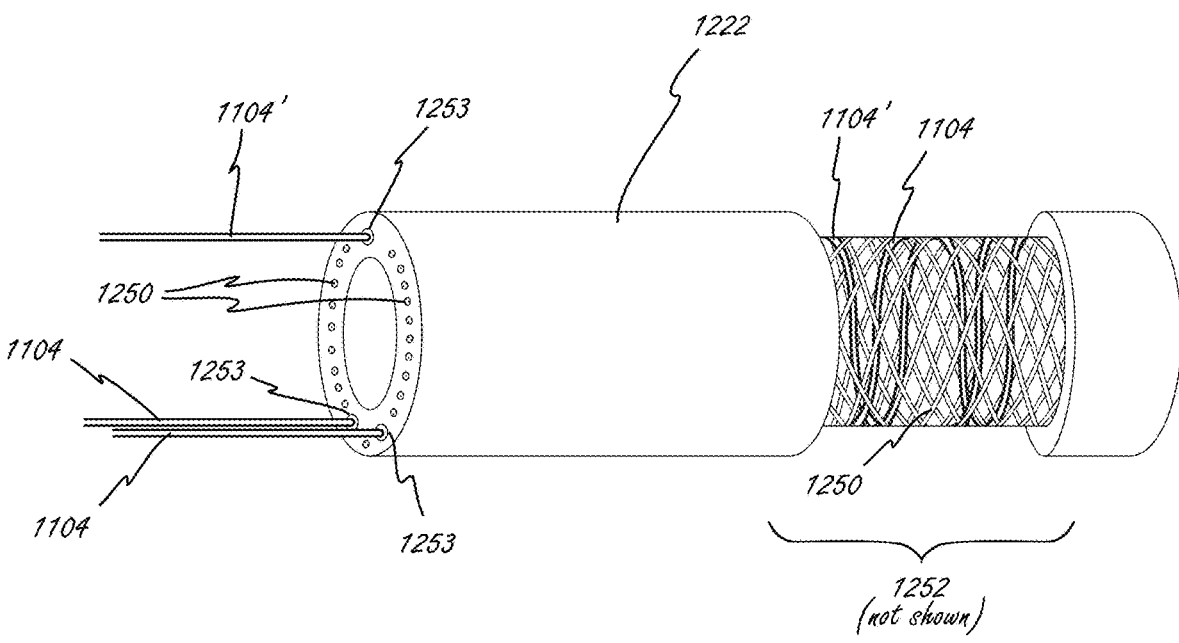
*Fig.* 3E

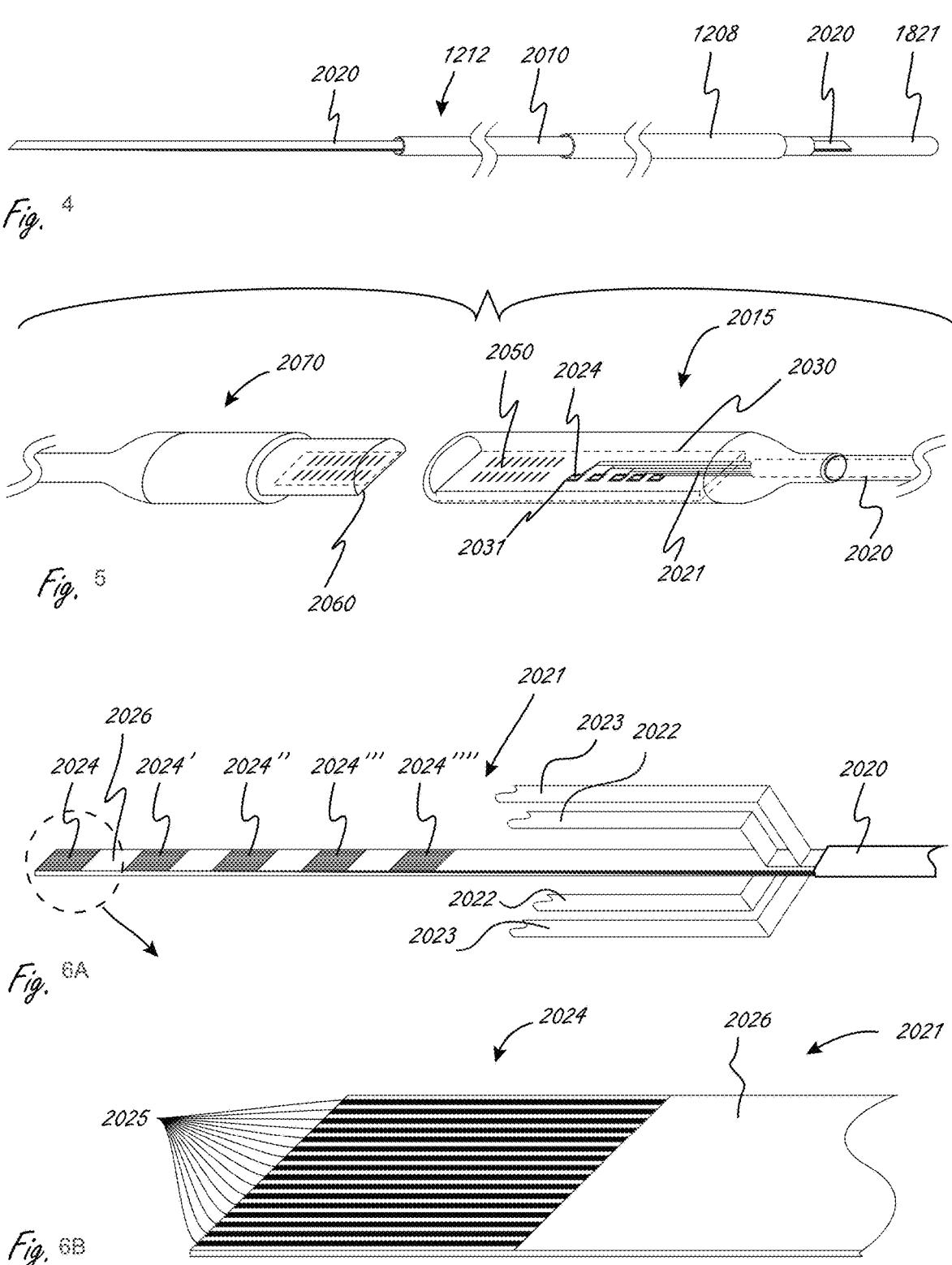
*Fig.* 4
*Fig.* 5
*Fig.* 6A
*Fig.* 6B

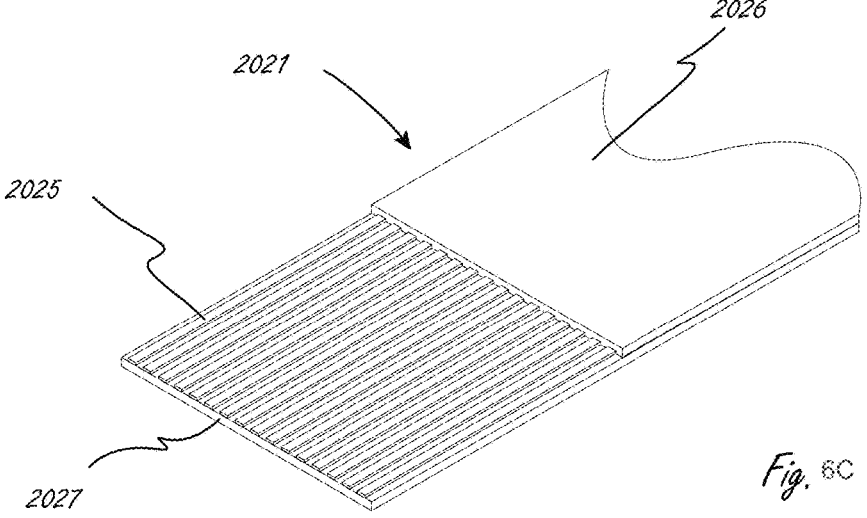
*Fig.* 6C
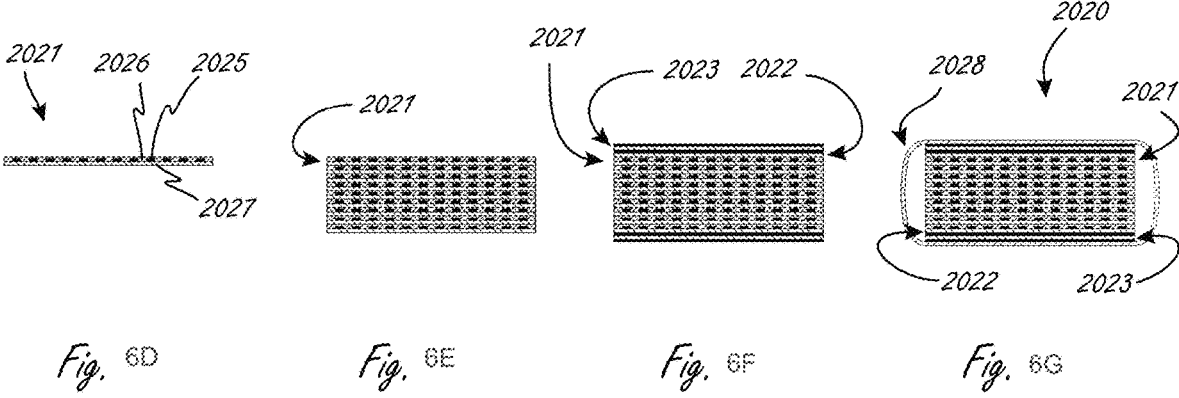
*Fig.* 6D　　　　*Fig.* 6E　　　　*Fig.* 6F　　　　*Fig.* 6G

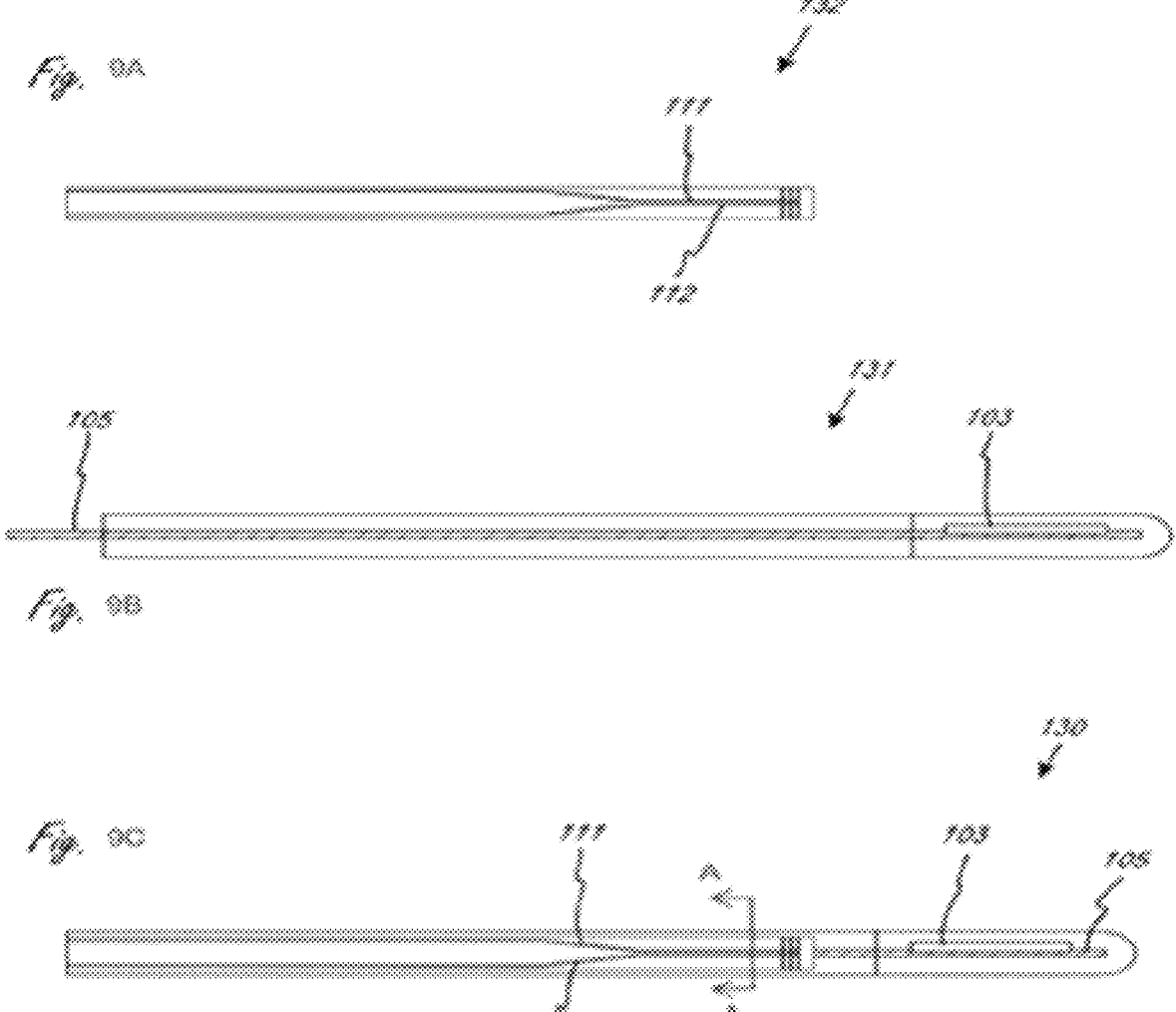

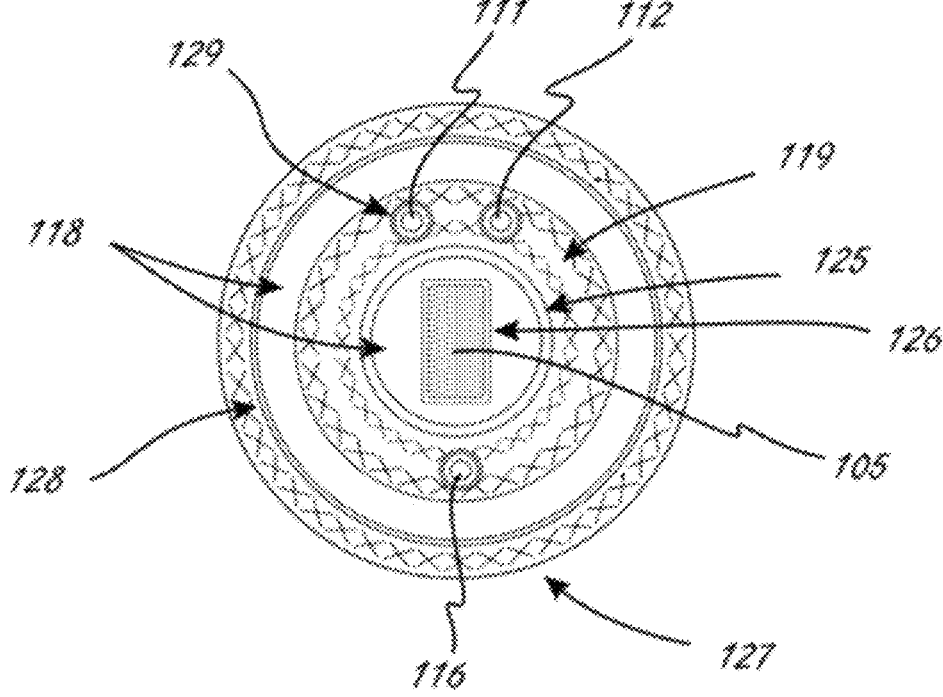
SECTION A-A
Fig. 9D

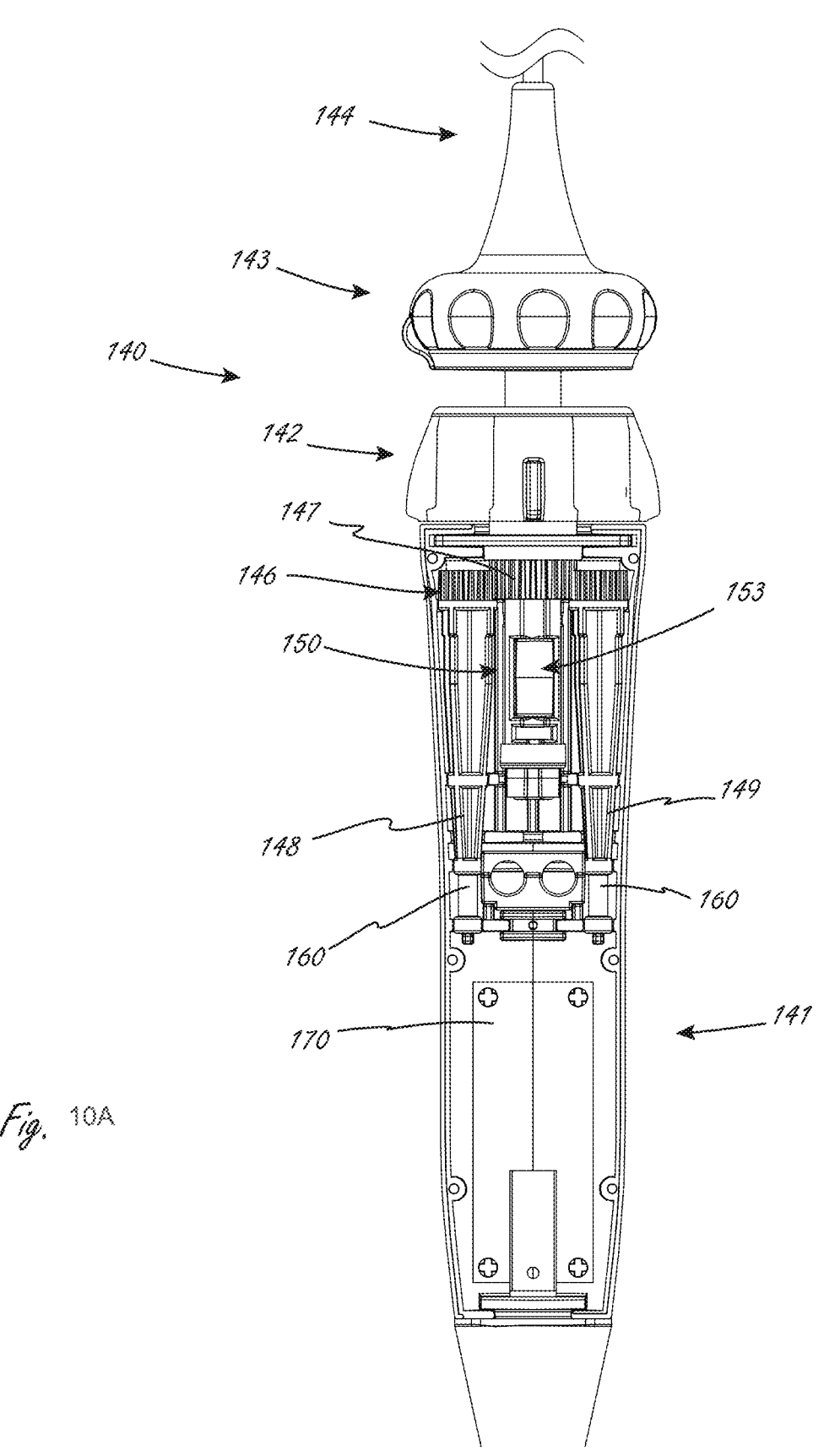
*Fig.* 10A

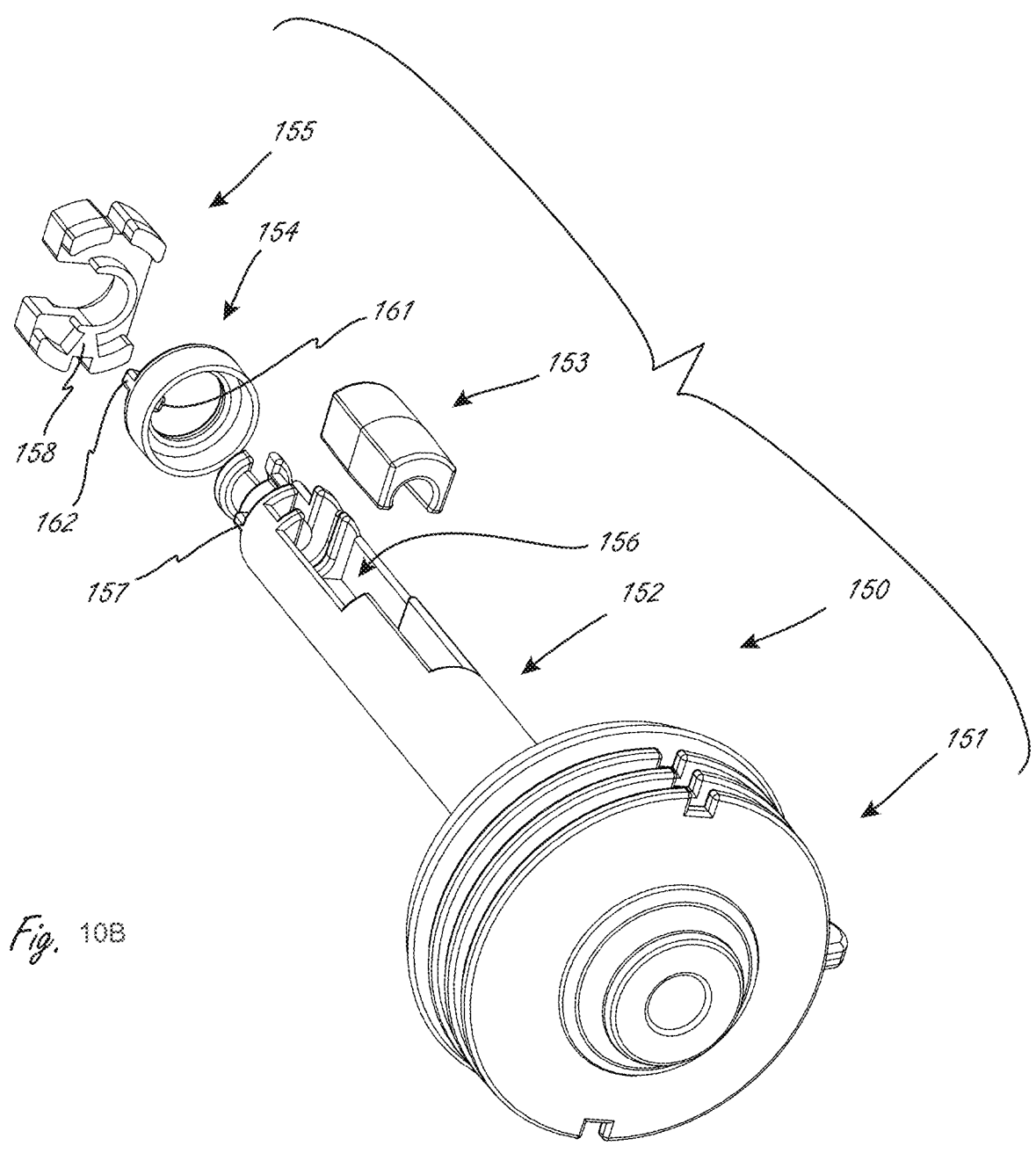
*Fig.* 10B

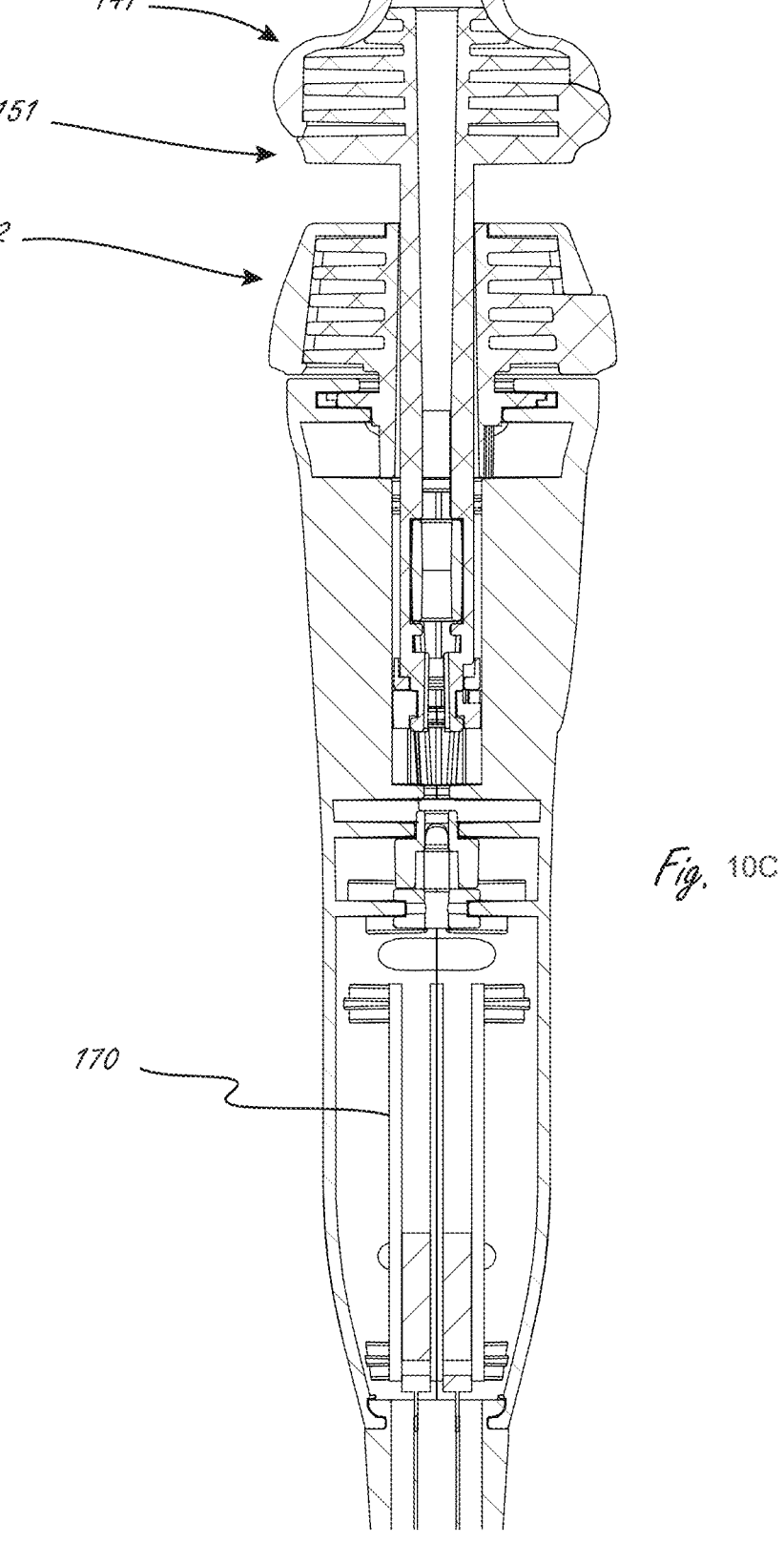
*Fig.* 10C

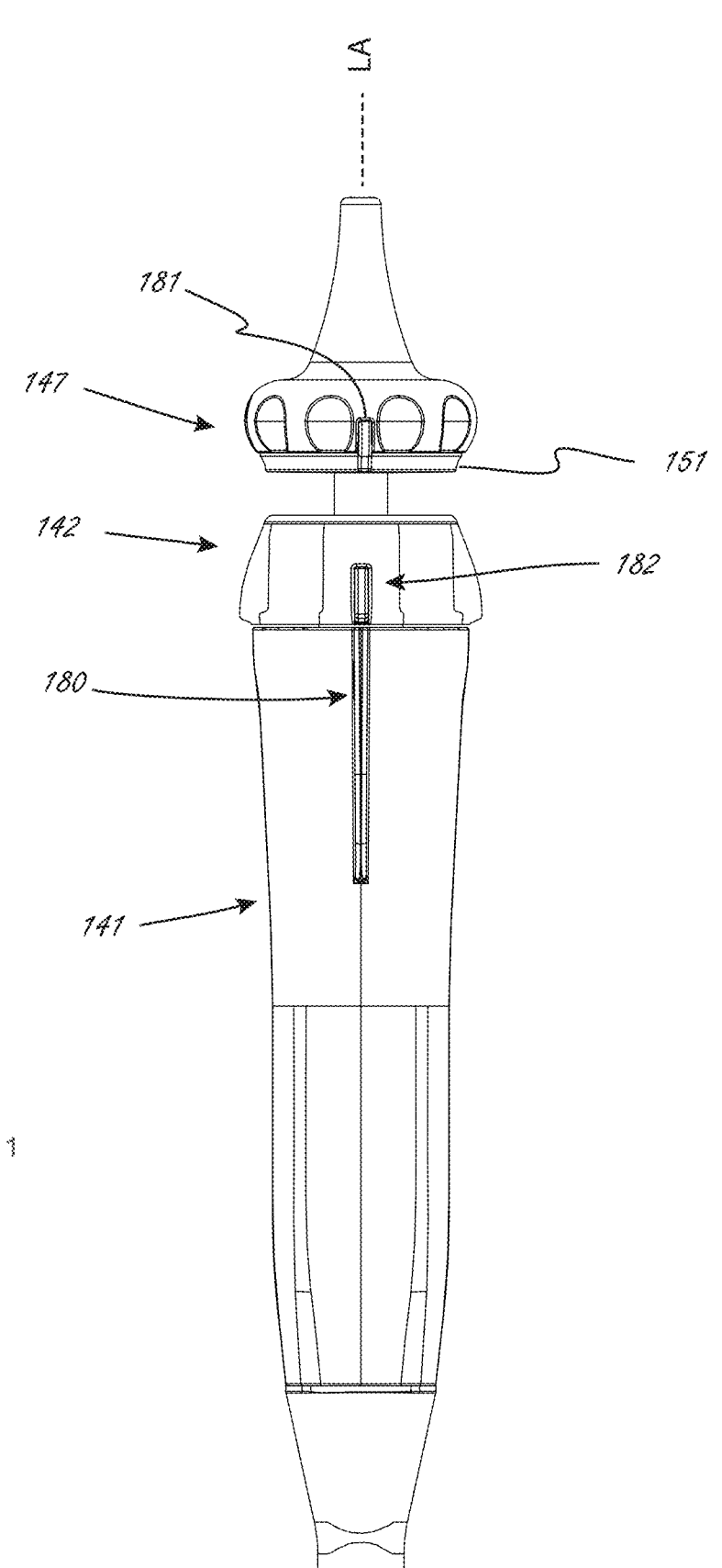
*Fig.* 11

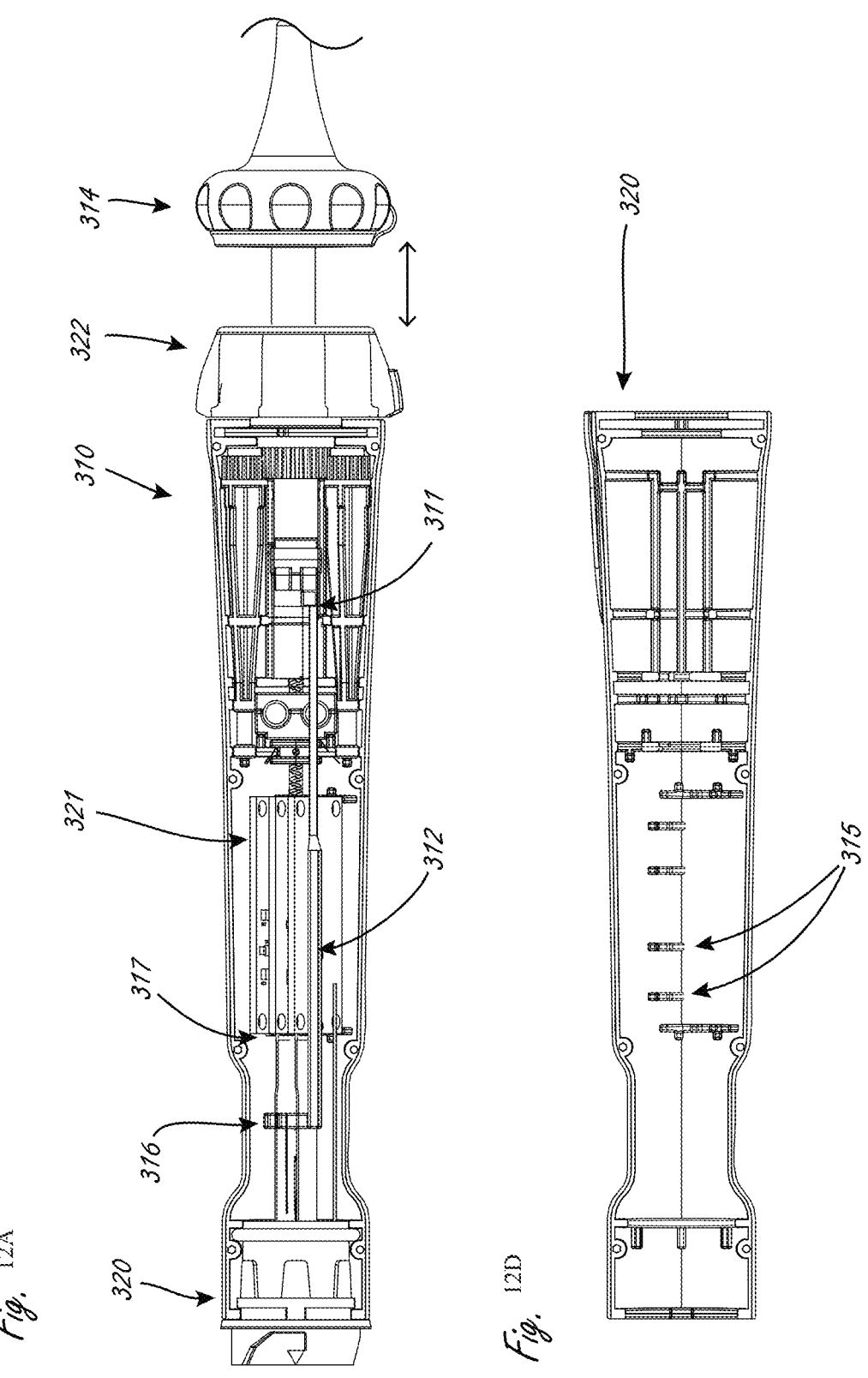
*Fig.* 12A
*Fig.* 12D

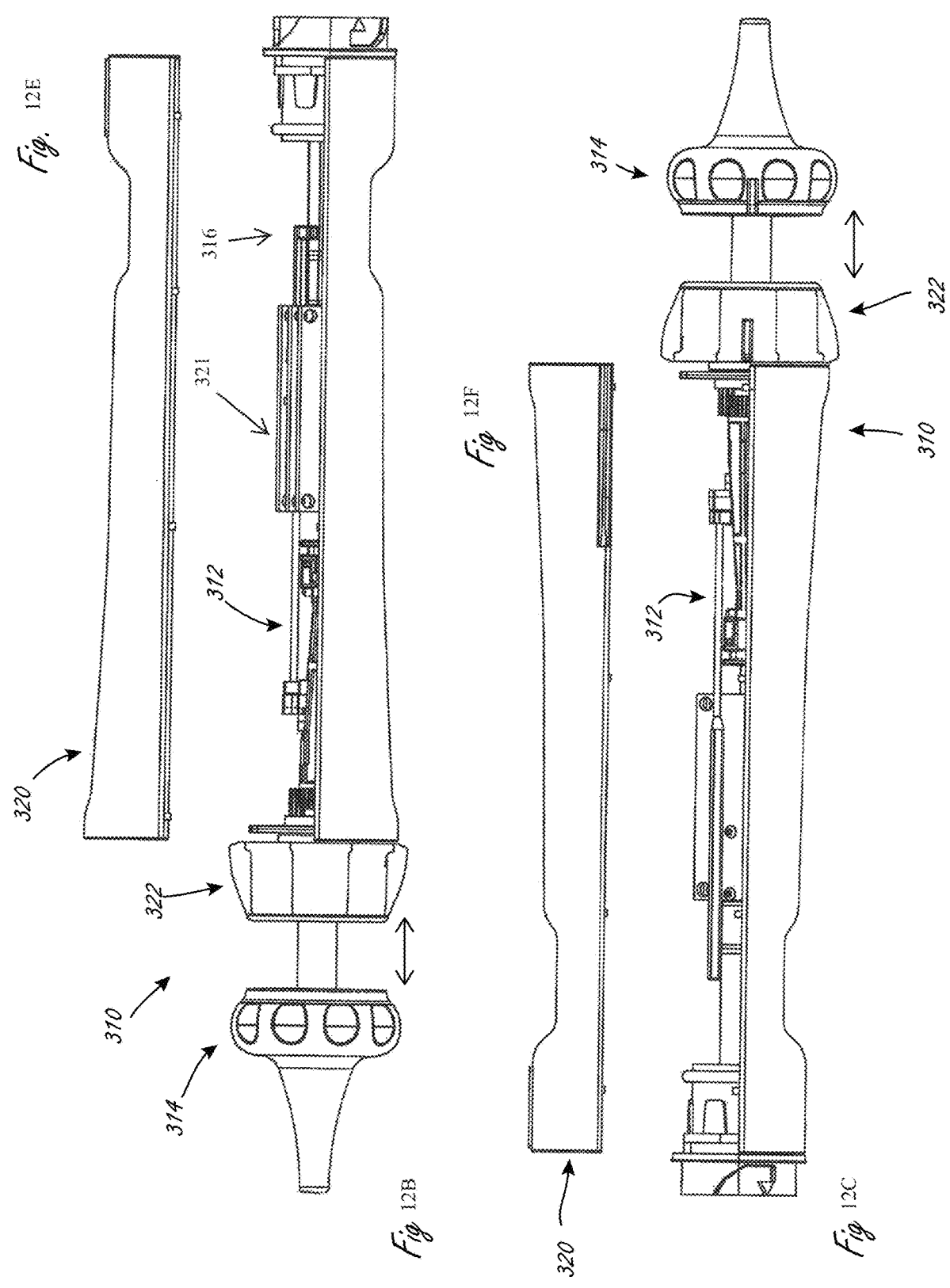
*Fig.* 12E
*Fig.* 12B
*Fig.* 12F
*Fig.* 12C

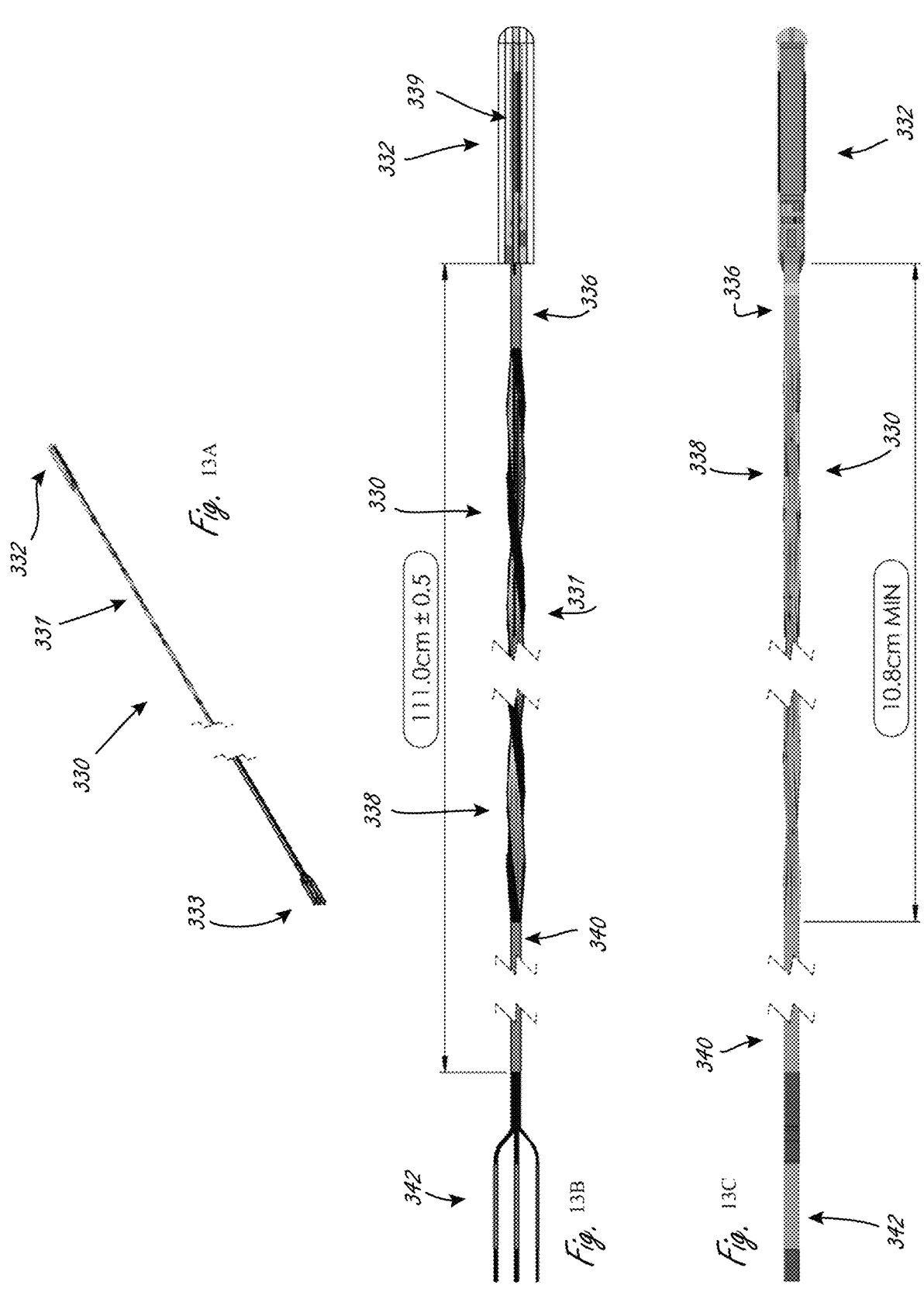
*Fig.* 13A
*Fig.* 13B
*Fig.* 13C

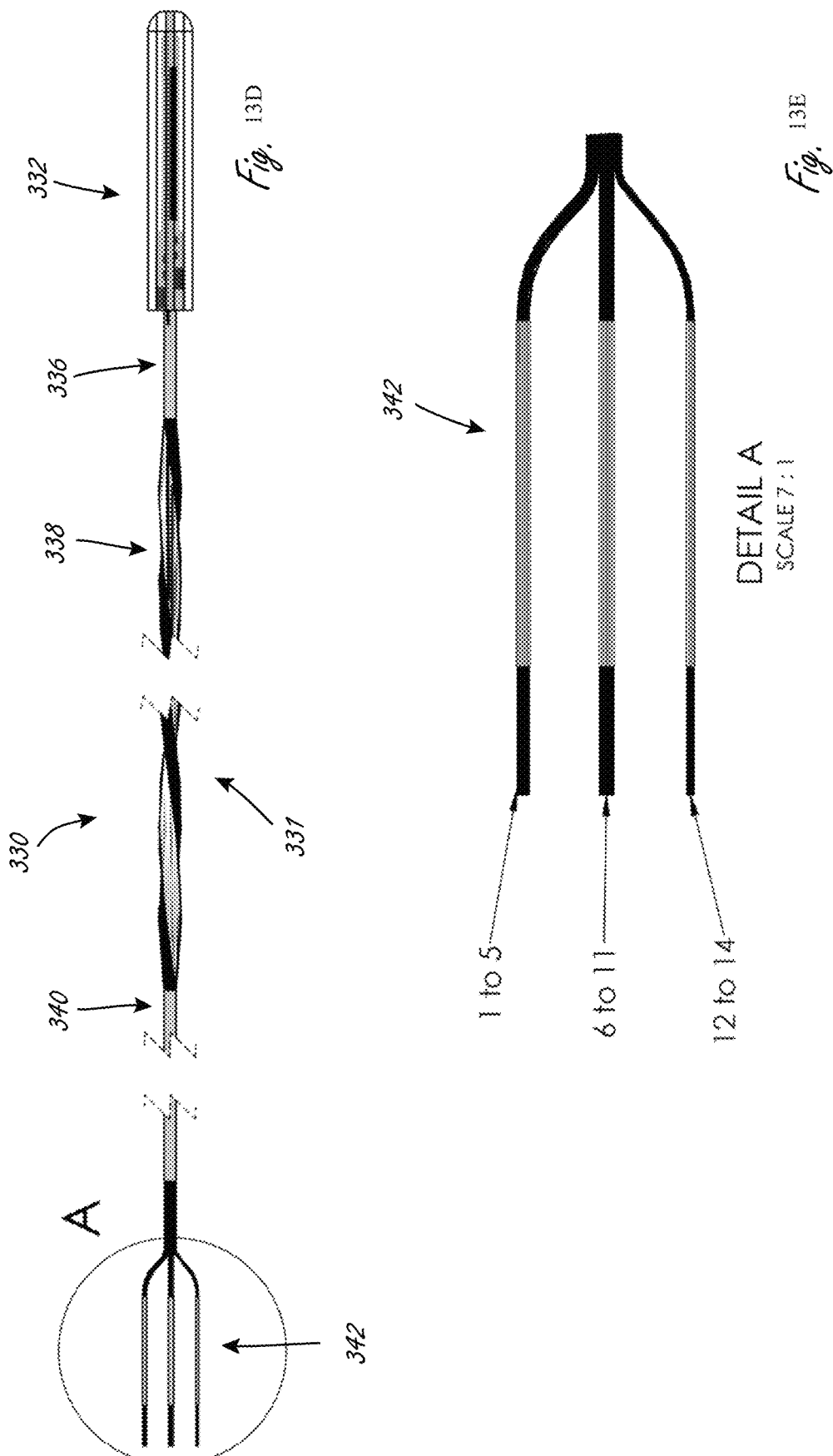
*Fig.* 13D
*Fig.* 13E
DETAIL A
SCALE 7:1
1 to 5
6 to 11
12 to 14

MEDICAL TOOL POSITIONING DEVICES, SYSTEMS, AND METHODS OF USE AND MANUFACTURE

INCORPORATION BY REFERENCE

This application is the national stage filing under 35 USC 371 of International Application No. PCT/US2020/030114 filed Apr. 27, 2020, which claims priority to U.S. Provisional Application No. 62/839,520, filed Apr. 26, 2019, which are incorporated by reference herein for all purposes.

This application incorporates by reference herein the entire disclosures of the following applications, which are incorporated by reference herein for all purposes: PCT/US2019/061228 filed Nov. 13, 2019; U.S. Prov. App. No. 62/760,784 filed Nov. 13, 2018; WO2018/017717, published Jan. 25, 2018; and WO 2018/182836, published Oct. 4, 2018.

All publications and patent applications mentioned in this specification are herein incorporated by reference to the same extent as if each individual publication or patent application was specifically and individually indicated to be incorporated by reference.

BACKGROUND

A wide variety of intravascular medical devices are known. Improved systems, devices, and methods that facilitate better control, positioning, and usability of medical devices are needed.

SUMMARY OF THE DISCLOSURE

The disclosure herein is related to medical devices and uses thereof. The disclosure is generally related to flexible elongate members (e.g., flexible conductor bundles) that may extend along some length of the medical device. Some aspects of the disclosure describe ways that prevent the flexible elongate members from deforming, or at least minimize the degree of the deformation. In some examples, the disclosure herein is related to trying to minimize bending along the flexible elongate member at one or more locations. While bending is a type of deformation, the disclosure may also be related to trying to minimize or prevent folding or otherwise bunching of the flexible elongate member. In some examples, the disclosure herein is related to trying to maintain a configuration of the flexible elongate member, or at least maintain the configuration as closely as possible to a certain configuration to try to prevent undesirable consequences of a large extent of deformation.

In some examples, a force is applied to a flexible elongate member at a location that is proximal to a location wherein the flexible elongate member is secured to a medical tool. The applied force may help prevent the undesired deformation and/or maintain the desired configuration.

One aspect of the disclosure is a medical device that is sized and configured to be positioned within a subject, such as within a blood vessel, chamber of the heart, or other bodily lumen or space.

The medical devices herein may include a medical tool such as an ultrasound transducer in a distal region of the medical device. The medical tool may be secured (directly or indirectly) to a flexible member(s), such as flexible electronics (e.g., a flexible conductor bundle) at a first location. The flexible member may extend proximally towards (and optionally into) a handle assembly. In some examples, the disclosure is related to trying to prevent the flexible electronics from deforming to an undesirable extent and/or trying to maintain a configuration of the flexible electronics (even if there some minor degree of deformation).

The medical device may include one or more elongate shafts through which the flexible member extends. The medical device may include more than one elongate shaft through which the flexible member extends, such as an outer shaft and an inner shaft, the inner shaft extending through at least a portion of the outer shaft. An inner shaft may be movable relative to the outer shaft. An inner shaft may be independently deflectable relative to the outer shaft.

The flexible member (e.g., flexible conductor bundle) may be axially movable within the one or more elongate shafts, and may be fixed to a shaft, such as an outer shaft.

The medical device may include a tensioning member secured to one or more surfaces of the flexible member (e.g., a flexible conductor bundle) at a second location that is proximal to where the medical tool is secured to the flexible member. The second location may be within a handle assembly of the medical device, but the second location may be distal to a handle assembly. The second location may be positioned such that it is within the subject when the medical device is in use.

A tensioning member may be in operative communication (operatively coupled) with handle assembly actuator (e.g., knob, etc.) such that actuation (e.g., rotating, moving axially) of the handle actuator causes movement of the tensioning member. The actuator may also be in operative communication with the medical tool. In some embodiments, the tensioning member and the medical tool are in operable axial communication with a handle actuator such that actuation of the handle actuator causes axial movement of the ultrasound transducer and the tensioning member. Axial movement of the tensioning may apply tension to the flexible conductor bundle at the second location within the handle assembly.

A tensioning member may be axially secured to a flexible conductor bundle at a second location within a handle such that the tensioning member and flexible conductor bundle move together axially at the second location upon actuation of a handle actuator.

A tensioning member may be secured to the flexible conductor bundle such that the flexible conductor bundle is maintained in a substantially flattened configuration, at least at a location near the medical tool. The flexible conductor bundle may be maintained in a substantially flattened configuration between the first and second locations when the medical tool is retracted proximally.

A flexible member may have flat or generally flat first and second surfaces, and a tensioning member may be secured to one or both of the flat or generally flat first and second surfaces.

An actuator may also be adapted to be rotated to cause rotation of the medical tool, and wherein a tensioning member and the actuator are in operative communication such that rotation of the actuator does not cause rotation of the tensioning member.

A flexible member (e.g., flexible conductor bundle) may be secured to a printed circuit board ("PCB") in the handle assembly, and optionally at a location that is proximal to the printed circuit board.

A medical device inner shaft may be in operable communication with a second handle actuator such that the inner shaft is deflectable upon actuation of the second handle actuator.

The medical device may include a flexible electronics (e.g., conductor bundle) flattening member secured to one or more surfaces of the flexible electronics at a second location, wherein the second location may be in a handle assembly. The flexible electronics flattening member and the medical tool may be in operable axial communication with a handle actuator such that actuation of the handle actuator causes axial movement of the medical tool and the flexible electronics flattening member, to thereby maintain the flexible electronics bundle in a flattened configuration, optionally between the first and second locations.

The medical device may also include a flexible electronics bend prevention member.

One aspect of the disclosure is a method of using a medical device that is configured and sized to be positioned within a subject. The method may include positioning an ultrasound transducer of an intravascular ultrasound catheter within a subject, wherein flexible electronics (e.g., a flexible conductor bundle) that are secured to the ultrasound probe at a first location extend proximally therefrom to a handle assembly; proximally retracting the ultrasound transducer; and applying tension to the flexible electronics at a second location that is proximal to the first location. The second location may be within the handle assembly.

The method may further comprise actuating a handle actuator, wherein actuating the handle actuator causes the proximal retraction of the ultrasound transducer and causes the application of tension to the flexible conductor bundle at the second location within the handle assembly.

Applying tension to the flexible electronics may prevent folding in the flexible conductor bundle distal to the second location.

Applying tension to the flexible electronics may comprise moving a tensioning member proximally within the handle assembly, the tensioning member secured to the flexible conductor bundle at the second location. The tensioning member may be in operative communication with a handle actuator, the method may further comprise actuating the actuator to cause the proximal movement of the tensioning member and the application of tension to the flexible conductor bundle.

The medical device may include flexible electronics that have a twisted configuration in a twisted region along at least a portion of its length.

BRIEF DESCRIPTION OF THE DRAWINGS

FIGS. 3Ai, 3Aii and 3Aiii illustrate an exemplary steerable shaft with pull wires.

FIGS. 3Bi and 3Bii illustrate an exemplary steerable shaft with pull wires.

FIGS. 3Di-3Diiii illustrate an exemplary steerable shaft with pull wires.

FIG. 3E illustrates an exemplary steerable shaft with one or more pull wires circumferentially interwoven into braid wires of the shaft.

FIG. 4 illustrates an exemplary portion of an exemplary system that includes a bundle.

FIG. 5 illustrates an exemplary proximal end of a medical tool, the tool including a conductor bundle that extends into a proximal connector within which is housed a printed circuit board (PCB).

FIG. 6A illustrates a portion of an exemplary medical tool that includes a flexible circuit strip.

FIG. 6B illustrates an exemplary proximal portion of a strip.

FIG. 6C illustrates a detailed view of an exemplary proximal portion of a strip.

FIG. 6D illustrates an end view of an exemplary flex strip.

FIG. 6E illustrates an exemplary stack of flex strips.

FIG. 6F illustrates an exemplary stack of flex strips and ground and shield strips.

FIG. 6G illustrates an exemplary bundle including a tubing material around a stack of strips and shield and ground strips.

FIG. 9A illustrates a portion of an exemplary inner elongate body, or inner shaft.

FIG. 9B illustrates a portion of an exemplary outer elongate body, or outer shaft.

FIG. 9C illustrates a portion of an exemplary medical device including the elongate bodies (or shafts) from FIGS. 9A and 9B.

FIG. 9D illustrates a section of the device in the deflectable portion from FIG. 9C.

FIG. 10A illustrates a portion of an exemplary handle assembly.

FIG. 10B is an exploded view illustrating an exemplary outer elongate body (or outer shaft) movement subassembly.

FIG. 10C illustrates a side sectional view of the handle assembly from FIG. 57A.

FIG. 11 illustrates an exemplary handle assembly that includes rotation indicators for first and second actuators.

FIG. 12A illustrates internal components of an exemplary handle assembly that includes a tensioning member, or flattening member.

FIG. 12B illustrates (in a side view) internal components of an exemplary handle assembly that includes a tensioning member, or flattening member.

FIG. 12C illustrates (in a side view that is the other side relative to FIG. 12B) internal components of an exemplary handle assembly that includes a tensioning member, or flattening member.

FIG. 12D illustrates internal components of an exemplary handle shell that include one or more guiding features positioned to help stabilize a tensioning member in the handle assembly.

FIG. 12E illustrates a side view of an exemplary handle shell.

FIG. 12F illustrates a side view of an exemplary handle shell.

FIG. 13A illustrates an exemplary flexible cable bundle with at least a portion that is twisted relative to a long axis.

FIG. 13B illustrates an exemplary flexible cable bundle with at least a portion that is twisted relative to a long axis.

FIG. 13C illustrates an exemplary flexible cable bundle with at least a portion that is twisted relative to a long axis.

FIG. 13D illustrates an exemplary flexible cable bundle with at least a portion that is twisted relative to a long axis.

FIG. 13E illustrates a detail from FIG. 13D.

DETAILED DESCRIPTION

Figures 1A, 1B:
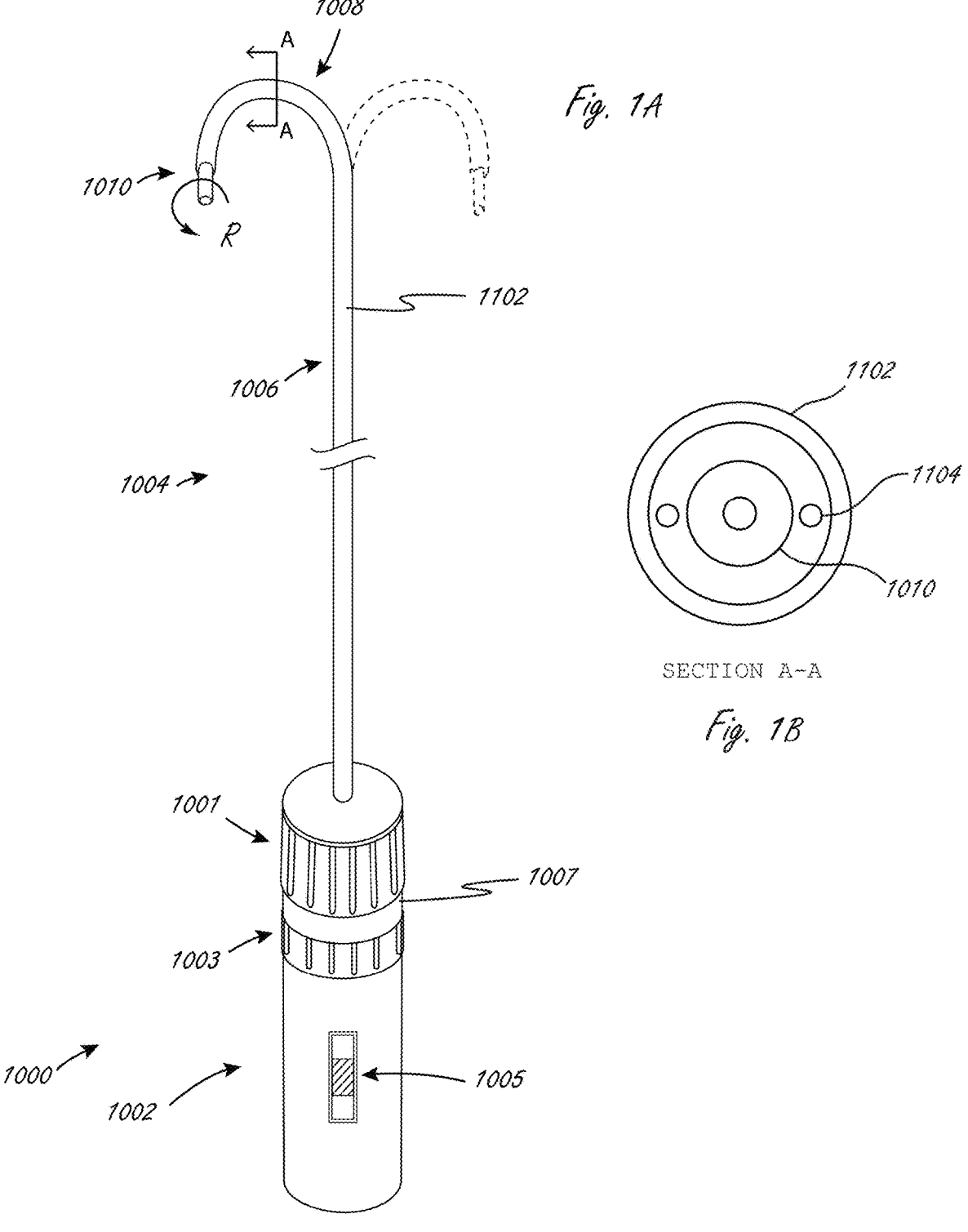
FIG. 1A illustrates an exemplary embodiment of a system that includes steering and a medical device.
FIG. 1B illustrates a cross section A-A of the steering and device portion of the medical device of FIG. 1A.

FIG. 1A illustrates an exemplary embodiment of a system that integrates steering and a medical device. System 1000 includes handle assembly 1002 and steering and medical device portion 1004. Steering and medical device portion 1004 includes a proximal portion 1006 and steerable portion 1008. The system is adapted so that handle assembly 1002 can be actuated to cause steering of the steerable portion 1008, and optionally can be further actuated to cause movement of medical device 1010 relative to steering and medical device portion 1004. In this exemplary embodiment, handle assembly 1002 includes first actuator 1001, second actuator 1003, and third actuator 1005. First actuator 1001 is adapted to be actuated (in this example rotated) relative to handle body 1007 to cause the steering of steerable portion 1008, and specifically steering outer sheath 1102. Steerable portion 1008 in this embodiment can be steered, or bent, into the configuration shown in FIG. 1A in solid lines, and can also be steered into the configuration shown in dashed lines, or anywhere in between, and in some embodiments the opposite steering function is limited to simply straightening the shaft from an initial bent configuration, such as the solid line bent configuration in FIG. 1A. The term "steer" in this disclosure means to deflect or bend, optionally via actuation of at least one pull wire, but in some instances the term can include shaft rotation (torqueing) and axial movement. The term "pull wire" herein refers to any element that may transmit a tensile force from the proximal end of the device to the distal end region. Pull wires may be comprised of metal wire such as stainless steel or nickel titanium, either solid or stranded/braided, or it may be comprised of a polymer such as aramid fiber (Kevlar®), polyethylene, ptfe, eptfe, etc., preferably stranded/braided, but also in monofilament form. In a preferred embodiment, the pull wire is constructed from an aramid fiber bundle having four 50 denier multifilament (approximately 25 filaments) threads braided together at a high picks per inch. The wire cross-sectional diameter is typically in the 0.005"-0.012" range, more preferably 0.008"-0.010", although braided or stranded wire may flatten or ovalize in the device lumen. The preferred construction embodiments are believed to provide optimized strength and wear resistance for the size necessary to keep the shaft diameters to a minimum. Optional second actuator 1003 is adapted to be actuated relative to handle body 1007 (in this example rotated) to cause rotation of medical tool 1010 relative to shaft 1102 (labeled as rotation movement "R"), and optional actuator 1005 is adapted to be actuated relative to handle body 1007 (in this example axially) to cause axial (distal-proximal) movement of medical device 1010 relative the outer sheath 1102. Proximal portion 1006 is not configured to bend significantly when steerable portion 1008 is steered (bent/deflected), although the proximal portion may flex and bend to conform to the anatomy within which it is used. In many embodiments, this is accomplished by constructing the steerable portion 1008 from a softer or less rigid material and/or composite construction than the proximal portion 1006.

The embodiment shown in FIG. 1A is an example of an apparatus that includes an integrated handle assembly that is in operable communication with both a steerable outer shaft and an inner medical tool. The handle assembly is integrated in that it is assembled and constructed to be in operable communication with the outer shaft and the inner medical tool prior to packaging and use. "Integrated" as that term is used in the context of an integrated handle assembly refers to a handle assembly in which at least one part of the handle assembly has to be broken or taken apart before the medical tool can be removed from within the outer shaft.

FIG. 1B illustrates an exemplary cross section A-A (shown in FIG. 1A) of the steering and device portion 1004, and specifically in the steerable portion 1008. In this embodiment medical device 1010 is sized and configured to be disposed within a steerable sheath. The steerable sheath includes an outer shaft 1102 and a set of pull wires 1104, which are axially fixed in a distal region of steerable portion 1008.

The medical tool in FIGS. 1A and 1B can be, for example, any medical tool herein, such as an ultrasound tool. When "ultrasound probe" is used herein, it generally refers to an elongate tool that includes at least one ultrasound transducer and one or more conductive elements that electrically connect the at least one ultrasound transducer to a proximal region of the elongate tool. A proximal region of the ultrasound probe includes, or is modified to include, at least one proximal contact, which is in electrical communication with the at least one ultrasound transducer, and which can be put into electrical communication with, optionally via attachment to, an electrical contact on another device, cable, or connector.

Figure 2:
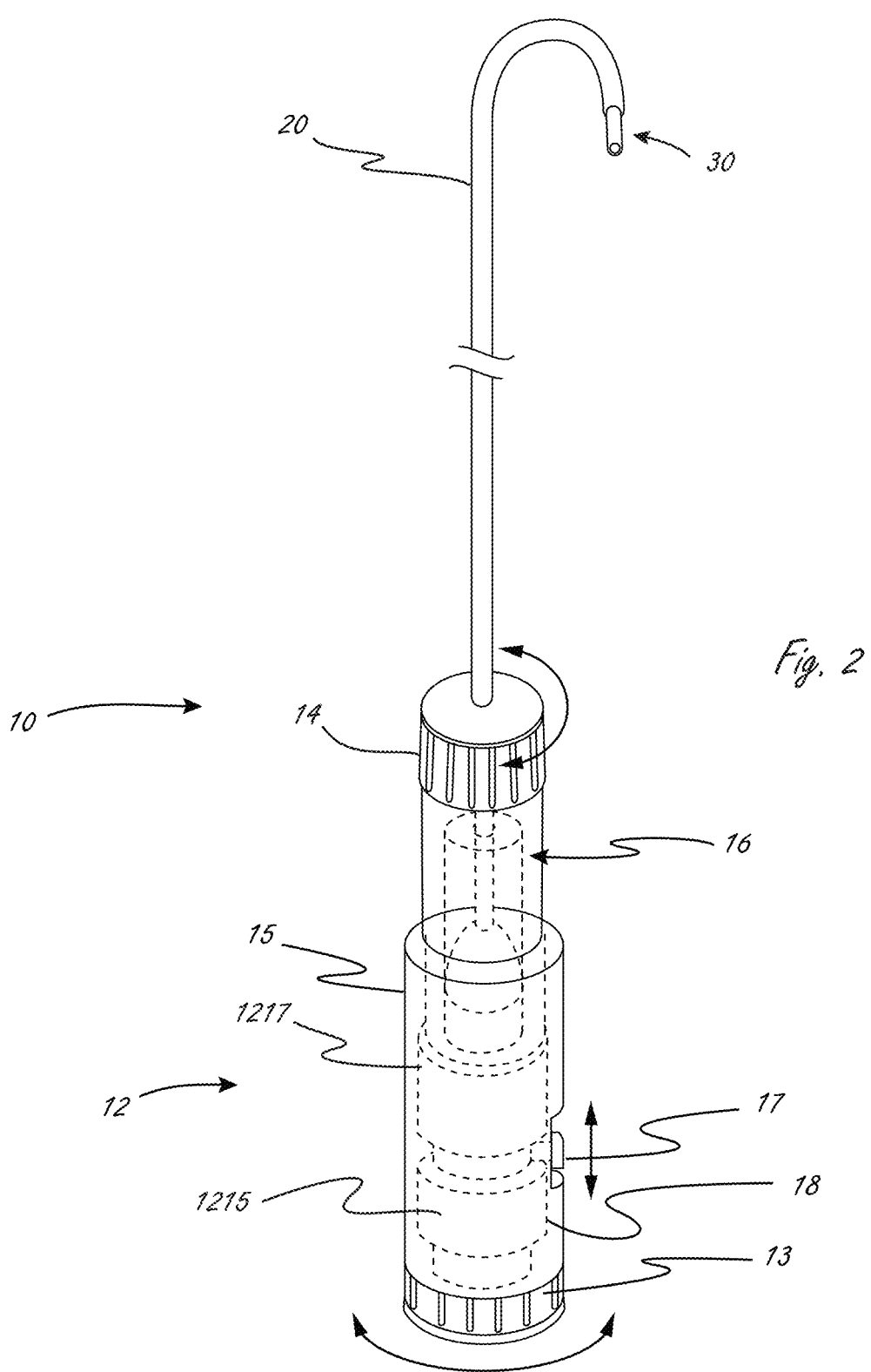
FIG. 2 illustrates an exemplary system that includes a handle assembly with a plurality of actuators, a steerable sheath and medical tool.

FIG. 2 illustrates an exemplary system 10 that is adapted to function similarly to the system in FIGS. 1A and 1B, and also illustrates exemplary internal components of handle assembly 12 (internal components shown as dashed lines). Handle assembly 12 is integrated and in operable communication with outer steerable shaft 20 and medical tool 30. Handle assembly 12 includes actuator 14 that is adapted to, when actuated relative to handle body 15, cause steering of steerable shaft 20. Actuator 14 is in operable communication with steerable shaft 20 via steering control 16 disposed in handle assembly 12. Medical tool 30 includes a proximal portion 18 disposed within and incorporated into handle assembly 12. Actuator 13 is in operable communication with medical tool 30, and actuation of actuator 13 (in this example rotation) relative to handle body 15, causes rotation of medical tool 30 relative to outer shaft 20 via rotation control 1215. Optional third actuator 17 is also in operable communication with medical tool 30, and is adapted to be actuated, in this embodiment, axially (relative to handle body 15), to cause axial movement of medical tool 30 relative to outer steerable shaft 20 via axial control 1217.

The medical tool in FIG. 2 can be, for example, any medical tool herein, such as an ultrasound tool.

Figure 3C:
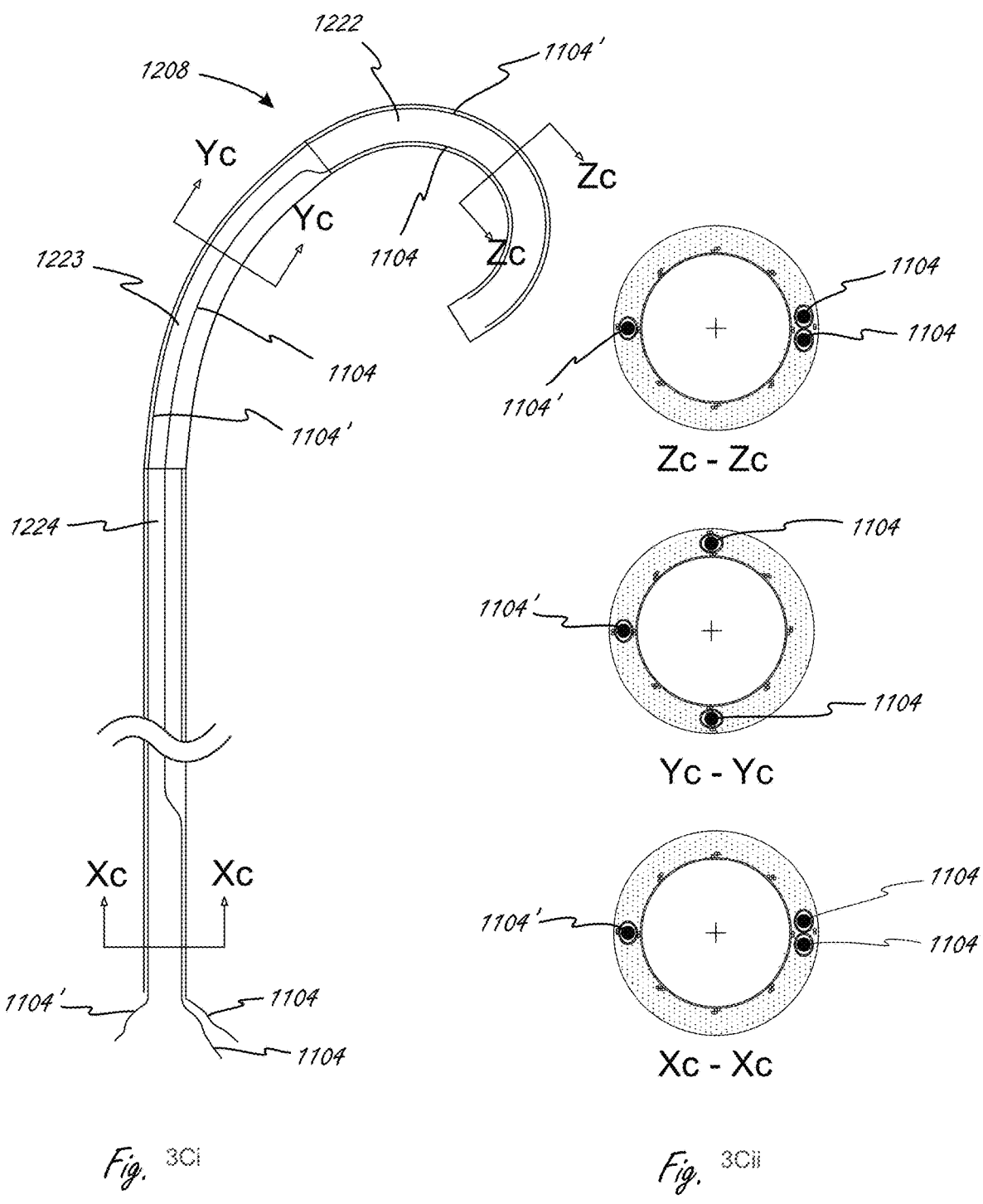
FIGS. 3Ci and 3Cii illustrate an exemplary steerable shaft with pull wires.

FIGS. 3A-3E represent exemplary embodiments of a distal region of the sheath portion 1208 of steerable sheath 1202 in system 1200. For simplicity, the illustrated cross-sections show only the outer sheath 1208 and not the inner tool 1212. The outer sheath 1208 preferably has a composite construction to improve torque transmission applied to the outside of the shaft from the proximal end, or to resist torque forces applied to it from within the shaft, such as from tool 1212. As illustrated in FIG. 3Ai-iii, in order to form the composite, multiple braid elements 1250, preferably formed from metal wire (round, pairs of round, or ribbon shaped) and/or multiple fibers (e.g., aramid or nylon), may be braided directly over a thin wall (e.g., 0.0010"±0.0005") lubricious liner tube 1251, such as a PTFE or FEP material. A thermoplastic polymer 1252 (such as Pebax in a range of durometers from 25 D-72 D, or nylon, or other common catheter materials) may be laminated with heat using heat shrink tubing (such as FEP) to reflow the polymer over the braid elements 1250 and liner tube 1251 to form a uniform member. The thermoplastic polymer 1252 may also have radiopaque compounds that include materials such as bismuth, barium sulfate, or tungsten in order that the tip of the sheath be visible to the user under fluoroscopy. In the embodiment of FIG. 3Ai-iii, the pull wire 1104 is preferably parallel to the central access in the steerable (deflectable) portion 1222 of the sheath and also preferably provided in a lumen 1253 created within the wall of the steerable sheath 1208. This lumen may be created during the thermoplastic polymer tubing extrusion process or during a shaft heat lamination fusing process with the aid of a removable mandrel. The pull wire lumen 1253 may further be created by incorporating a pull wire tube 1254, preferably temporarily supported by a removable mandrel, within the wall. The removable mandrel may also be placed alongside the pull line 1104 or 1104' during the fusing process, resulting in a somewhat ovalized lumen 1253 within which a fiber pull wire may be allowed to flatten into, allowing space for free movement of the pull wire. The tube 1254 may include PTFE, FEP, polyimide, or another material which maintains its wall integrity during a heat lamination process up to approximately 500° F. The tube is preferably surrounded and supported by the thermoplastic polymer 1252 which is preferably heat laminated against the tube. In another embodiment, the pull wire lumen, preferably comprising the pull wire tube, is incorporated within the weave of the braid elements 1250. For example, braid elements 1250 running in one direction would pass under the pull wire lumen, while those running in the opposite direction would pass over the pull wire lumen. The braid reinforcement provides a more dimensionally stable lumen during catheter manipulations and also helps assure the straightness of the lumen as needed. Proximal to the steerable portion, the pull wire may continue proximally parallel to the central axis on the same side of the outer sheath 1208, such as is illustrated in FIG. 3Ai-iii. In this embodiment and others that follow, an additional pull wire 1104' within an additional pull wire lumen routed within the wall of sheath 1208, up through the steerable portion 1222, may be required to straighten the steerable portion of the device. This straightening pull wire 1104' is preferably routed within steerable portion 1222 on the side opposite from the pull wire(s) 1104 used for steering (deflection) in the steerable portion 1222. In another embodiment, not shown, two lumens and two straightening pull wires 1104' could be used, essentially mirroring the paired 1104 pull wire configuration. These straightening wires could also be constructed to allow deflection in the opposite direction by tensioning a greater distance (beyond just straightening) within the handle.

During use, a portion 1223 of the distal catheter just proximal to the steerable (deflectable) portion 1222 may be forced to conform to a curve based on the constraints of the anatomy in which it is used. For a specific embodiment where the device is advanced into the heart chambers from a groin access, the portion 1223 forced into a curve is expected to range from 5 to 25 cm in length. During rotation of the sheath shaft 1208 from the proximal end, torque is transmitted through this distal curved region 1223 to the catheter tip. A non-uniform cross section and/or tension of the device in this region 1223 may induce a tendency for the shaft to build up and suddenly release torque, causing a "whip" or sudden jerk in rotation as it is torqued. To minimize the potential for whip, it is optional to distribute the pull wire tension and construction material around the surface of the curved region 1223. In one embodiment, such as is illustrated in FIG. 3Bi-iii, the pull wire 1104 may spiral around the central axis of the sheath in at least the curved region 1223 proximal to portion 1222. The pull wire of this embodiment may make a full circumferential wrap over approximately 10 cm of length, with this value ranging 5-15 cm. The spiral may only need to be present in the curved region 1223, continuing straight proximally thereafter through proximal portion 1224 (similar to 1006), which may minimize the friction in the pull wire lumen and the associated pull wire force required to steer (deflect) the steerable portion 1222. The spiral may also make a minimum of one turn before continuing straight, or spiral the full length of the shaft. In another embodiment to minimize whip, it may only be necessary to distribute the pull wire tension to opposite sides of the shaft. As illustrated in FIG. 3Ci-ii, deflection of the steerable section 1222 is accomplished with two parallel pull wires 1104 positioned adjacent one another on the same side of the sheath 1208. In the curved region 1223 and proximal portion 1224 (similar to 1006) proximal to the steerable section 1222, the pull wires are routed to opposite sides of the shaft, each 90° from the position in the steerable section 1222, to distribute the tension more evenly. While it is preferable to actuate the two parallel pull wires at the same time with equal force with the handle actuator, in other embodiments, a differential in force could be applied to steer the tip to one side or the other of the plane formed when the two are actuated with equal force. In other embodiments, any plurality of pull wires could be routed in the same configuration as illustrated in FIGS. 3B or FIG. 3C, with the multiple proximal pull wires distributed uniformly around the shaft circumference. Also, as illustrated in FIG. 3Ci-ii, the pull wires 1104 may be routed proximally along the opposite sides of the shaft for most of the shaft proximal portion 1124 length, but preferably brought back together adjacent one another near the proximal end portion of the shaft to allow the wires to exit the same side of the proximal shaft together to facilitate them being secured together to a handle component for simultaneous actuation tension.

FIGS. 3Di-iv illustrate another embodiment of the distal region of catheter with construction similar to that previously described, but instead configured to provide a distal steerable portion 1222 which can be deflected into two different directions. As illustrated, a two pairs of pull wires 1105/1107 and 1106/1108 are along the proximal shaft region 1224 and curved region 1223. This is similar to FIG. 3Ai-iii, except that the wires are paired on each side of the shaft. The routing could also be spiraled as in FIG. 3Bi-ii, or other configurations discussed. Within distal steerable portion 1222, the wires are routed 90° from the proximal portions, although other angles are contemplated. At a junction 1225 within 1222 one or more of the pull wires (e.g., 1105 and 1107) may be terminated and anchored to the shaft, with the remaining pull wires (e.g., 1106 and 1108) continuing to a more distal tip location 1226 where they are anchored. This configuration allows independent actuation of pull wires terminated at 1225 and 1226 such that different shapes may be created during actuation. FIG. 3Dii shows both lines 1107 and 1108 tensioned to create a variable curve in the same direction. FIG. 3Diii shows lines 1107 and 1106 tensioned to create an "S" curve. Other configurations are also possible.

The pull wires (such as 1104 and 1104') must be terminated at their distal end in a manner that reliably affixes them to the wall of the distal steerable shaft portion 1222, such that they do not break or pull free under repeated applications of tension. In a preferred embodiment, shown in FIG. 3E, the pull wires 1104 and 1104', upon exiting the distal pull wire lumen 1253, are circumferentially interwoven into the braid wires 1250 of the distal shaft 1222 (shown without the thermoplastic polymer 1252). One or more of the pull wires 1104 or 1104' may also be additionally or instead wrapped and/or tied around the outside of the braid wires 1250 for additional securing. The braid wires 1250 may be then trimmed distal to the securing point, with the interwoven and/or wrapped pull wires preventing the braid wires from expanding and/or unraveling. Additional adhesives such as UV cured or cyanoacrylates may also be used to secure the pull wires to the braid wires. The weave and/or wrap of the pull wires and braid wires is then laminated with a thermoplastic polymer which melts within the space around the wires and cools to secure them in place. The thermoplastic polymer may also have radiopaque compounds that include materials such as bismuth, barium sulfate, or tungsten in order that the tip of the sheath be visible to the user under fluoroscopy.

In additional embodiments, the tool 1212 may also or alternatively be constructed with one or more pull wires to deflect the tip in a manner similar to any of the previous embodiments described for the outer sheath 1208. In addition to routing the pull wires within the wall of the tubular member of the tool 1212, the pull wires could be routed next to the conductors inside the lumen of the tubular element 1212. Actuation of the pull wires could be from an actuator located in the proximal handle 1206. The distal shaft of tool 1212 may also be formed into a particular shape (e.g., an arc) such that it bends into the shape as it exits the tip of the steerable portion 1222 of outer sheath 1208. The stiffness of the distal shaft of tool 1212 is such that it does not substantially deform outer sheath 1208 while inside, but upon exiting is allowed to bend. The shape may be set by any one or combination of the following means: heat setting the polymeric material, using a moveable or fixed shaped stylet within the inner lumen of shaft 1212 or within a lumen within the wall of shaft 1212. Such a stylet could be round, oval, or rectangular in cross section, and be formed of stainless steel, nitinol, or a rigid polymer such as PEEK, Vestamid, or similar. The outer steerable sheath could alternatively be made to bend with a similar method as above, with or without additional pull wire deflection, and with or without additional shape or deflection of the distal portion of tool shaft 1212.

One aspect of the disclosure includes methods of disassociating at least a portion of the system from other components, optionally as part of a reposing process. In some embodiments the medical tool includes one or more electrical contacts that are coupled to other electrical contacts, which are in electrical communication with an energy console, and examples of consoles are known in the ultrasound art.

FIG. 4 illustrates merely a portion of an exemplary medical tool, such as an ultrasound probe, that can be electrically coupled directly or indirectly to an energy console, such as an ultrasound console.

Reposing the device can involve disconnection of one or more proximal electrical contacts and moving the tool portion distally out of the distal end of the sheath portion. In this embodiment tool portion 1212 comprises at least a tool outer sheath or member 2010, distal working end 1821 (which can include at least one ultrasound transducer), and conductor bundle 2020. The conductor bundle 2020 extends from the distal working end 1821, through the tool outer member 2010 to a proximal connector (the connector and handle mechanism are not shown in FIG. 18 for clarity). In some embodiments the medical tool is used for ultrasound imaging, optionally where the distal working end 1821 comprises a two-dimensional (2D) array of piezo electric components mounted on an ASIC (application specific integrated circuit).

FIG. 5 illustrates a merely exemplary proximal end of a medical device (the medical device is shown on the right), and in this embodiment the medical device is an ultrasound probe. The proximal end 2015 of the medical device is adapted to be electrically coupled to connector cable 270, which is directly or adapted to be indirectly electrically coupled to an energy console, such as an ultrasound energy console. As illustrated in FIG. 5, flexible conductor bundle 2020 extends from a distal region of the medical tool (distal region not shown) into a proximal connector 2015 within which is housed a rigid or flexible printed circuit board ("PCB") 2030. The connector bundle 2020 includes a plurality of contacts 2024 (examples of which are described below) that are attached to PCB board contacts 2031. Each individual trace from each contact 2031 is linked to individual exposed contacts 2050 on another portion, optionally more proximal, of the PCB. The individual PCB traces may also pass through other useful circuitry on the PCB. The exposed contacts 2050 are configured for a mechanical mating for electrical conduction to similar contacts 2060 on mating connector cable 2070, similar in concept to the proximal tool connector 1990 described previously, which links the tool 1204 to a user-interface console. Proximal connector 2015 can be incorporated into any of the systems, handles, steerable sheaths, medical tools, etc., herein.

"Conductor bundle" as that term is used herein may be interchangeably used with "flexible conductor bundle" unless indicated to the contrary herein.

FIGS. 6A and 6B illustrate an exemplary conductor strip (also referred to herein as a flexible circuit strip) 2021 that can be included in any of the conductor bundles herein. The embodiment in FIGS. 6A and 6B is an example of a conductor strip that can be included in bundle 2020 from FIGS. 4 and 5. The embodiment in FIGS. 6A and 6B can be incorporated into any other system herein.

As shown in FIGS. 6A, 6B and 6G, conductor bundle 2020 comprises a plurality of flex circuit strips, including multi-trace strips 2021, as well as conductive strips for grounding 2022 and shielding 2023 (only a portion of which are shown). Each multi-trace strip comprises a plurality of conductive traces 2025, which can be seen clearly in FIGS. 6B, 6C and 6D. The number traces 2025 in FIGS. 6D-G is twelve, and the number of traces in FIGS. 6A-6C is sixteen, and they are both exemplary as to the number of traces 2025 that can be used. Each strip 2021 can be approximately 0.072" wide and 0.0022" thick, and can optionally comprise sixteen 0.0022" widexabout 0.0007" thick conductive (e.g., copper) traces, each spaced approximately 0.0022" apart. The traces are disposed on an insulating substrate layer 2027, such as a polyimide substrate, and the traces can be at least partly covered by a cover layer 2026, such as a photoimageable film cover ("PIC") layer or other dry film solder mask (DFSM) or other similar material. The cover layer generally extends along most of the bundle, except at discrete locations in proximal and distal regions for electrical coupling. In other embodiments, the strip 2021 is approximately 0.055" wide and comprises twelve conductive traces (see FIGS. 6D-G). In other embodiments, the strip 2021 is approximately 0.037" wide and comprises eight copper conductive traces. The outer strips 2022 and 2023 used for grounding and shielding may have a similar construction and dimension except they can comprise a single full width strip of copper. As optimized for a 2D piezo array, a stack of approximately seven 16-trace strips 2021 would be required (or nine 12-trace, or fourteen 8-trace), along with one each of strips 2022 and 2023 on each side of the stack of multi-trace strips. FIG. 6E illustrates a portion of an exemplary bundle 2020 with nine strips 2021 stacked together. FIG. 6F illustrates a portion of the bundle that includes nine strips 2021 stacked, as well as ground strip 2022 and shield strip 2023 (only those on top are labeled). The complete bundle may optionally be held together with a, for example without limitation, about 0.001" wall thickness shrink tube, such as the tubing 2028 in FIG. 6G. The flex circuit dimensions and number of traces discussed above are for a particular configuration of a piezo-electric array (and/or an ASIC controller thereof) and may be varied depending on how the number and size of array elements are optimized for the particular application.

The proximal end of each flex circuit strip has the conductive material (e.g., gold-plated copper) exposed over a length of approximately, for example, 3 mm through removal of the cover layer 2026 at location 2024. Location 2024, and other exposed locations 2024', 2024" 2024"', 2024" described herein, is generally referred to as a "contact." It is understood that when used in this context, the contact actually includes a plurality of separated conductive traces (such as shown in region location), each of which is adapted to be in electrical communication with its own corresponding conductive element. "Contact" is therefore not limited to mean only a single electrical connection between two conductive elements. While FIG. 6A shows a plurality of exposed regions 2024, the embodiment in FIG. 6A will first be described herein as if there is only one exposed region (i.e., region 2024 at the proximal end). The strip 2021 can be made to create an electrical connection to matching exposed contacts 2031, shown in FIGS. 6A-C, for conductive traces on the PCB 2030. In some embodiments, sixteen individual traces, sized and spaced to match sixteen traces in the multi-trace strip 2021, would be provided within a given contact 2031. An ACF (anisotropic conductive film), soldering, conductive adhesive, mechanical connection, or any combination of these may be used to achieve a suitable electrical connection (electrical coupling) between the strip traces and the PCB contacts.

Figure 7:
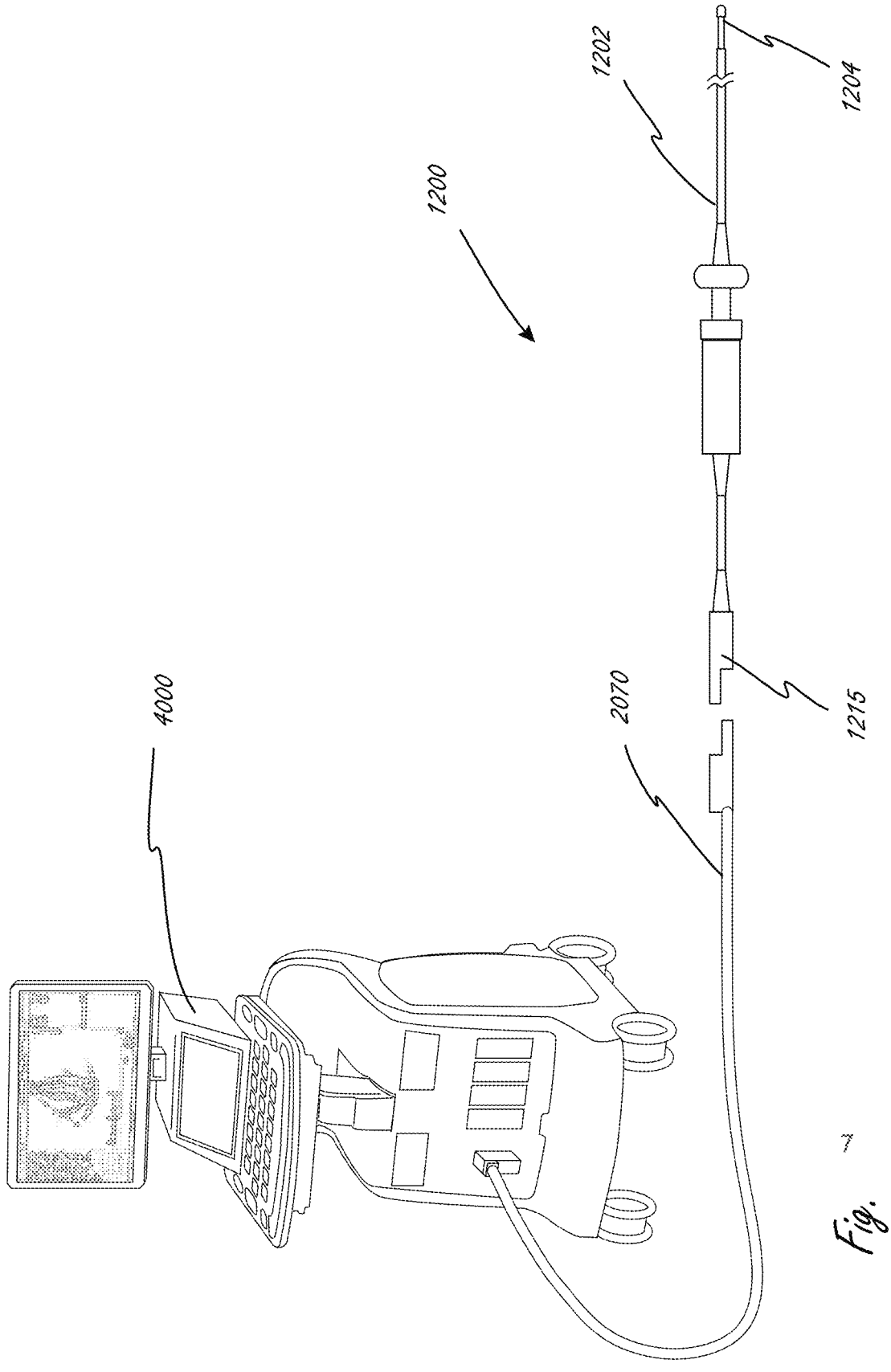
FIG. 7 illustrates an integrated system of the steerable sheath and medical tool wherein the system is connected to a console via a connector cable.

FIG. 7 illustrates the integrated system 1200 of the steerable sheath 1202 and medical tool 1204 wherein the system 1200 is connected to console 4000 via the connector cable 2070. As previously described, such as for FIG. 5, the tool 1204 comprises a proximal connector 2015 which forms a mating connection to cable 2070. As previously described, it is desirable to repose (e.g., reprocess and reuse) the system 1200. It is further desirable to ensure that the system is reposed only by the original manufacturer and not an unaffiliated third-party, and to ensure the device is only reused a specified number of times. To control the reposing process, a crypto-authentication chip (crypto-chip) is incorporated into the tool 1204, preferably on the PCB 2030, although other locations, such as within the steerable handle 1206, or within the tip 3000, are contemplated. The crypto-chip is programmable only by the original manufacturer who controls the authentication keys. The console 4000 to which the system 1200 is connected has a Trusted Platform Module (TPM) which also has the authentication keys. During use of the system 1200, the console 4000 is able to authenticate the system 1200 via the crypto-chip and as desired may read and write information to the chip (e.g., via an EEPROM feature). In any of the scenarios discussed, RFID chips, preferably encrypted, may be used to read and transmit data between the console, connector, and the device.

As used herein, "cleaning" can refer to any type of cleaning, such as without limitation: cleaning an interior of an outer shaft using a flushing system of cleaner and/or disinfectant and optionally mechanical scrubbing with small brushes; mechanical cleaning (e.g., wipes, brushes) an outer portion of an outer shaft and/or outer portion of a medical device shaft (e.g., ultrasound probe) with a cleaner/disinfectant, and optionally submerging the shaft in an ultrasound bath of cleaner/disinfectant for a specified period of time; and optical cleaning methods such as comprising using UV light. "Cleaning" as used here does not refer to a specific cleaning process, but rather refers to the general idea of cleaning an object.

The disclosure herein also includes methods of assembling or reassembling any of the subassemblies or assemblies herein, including any of the subassemblies within any of the handle assemblies herein. For example without limitation, the disclosure here includes methods of spooling one or more pull wires over a bearing surface in a spindle support and then around the spindle.

The methods herein also include manufacturing or constructing any of the individual components of any of the subassemblies or assemblies herein. For example, the disclosure includes methods of manufacturing handle shell components that have particular configurations (e.g., guides, walls, etc.) that can accommodate the internal parts that allow the assemblies or subassemblies herein to function as intended.

Regardless of the reference number with which they are labeled, any of the handle assemblies, medical tools, steerable sheaths, and electrical connections herein can be used together in a system in any combination with each other.

Any of the technology, including ultrasound and steering technology, in any of the following U.S. patent references may be incorporated into any of the medical tools, devices, systems, or methods of use thereof herein, the disclosures of which are incorporated by reference herein: U.S. Pat. Nos. 6,100,626, 6,537,217, 6,559,389, 7,257,051, 7,297,118, 7,331,927, 7,338,450, 7,451,650, 7,451,650, 7,527,591, 7,527,592, 7,569,015, 7,621,028, 7,731,516, 7,740,584, 7,766,833, 7,783,339, 7,791,252, 7,791,252, 7,819,802, 7,824,335, 7,966,058, 8,057,397, 8,096,951, 8,207,652, 8,207,652, 8,213,693, 8,364,242, 8,428,690, 8,451,155, 8,527,032, 8,659,212, 8,721,553, 8,727,993, 8,742,646, 8,742,646, 8,776,335, 8,790,262, 8,933,613, 8,978,216, 8,989,842, 9,055,883, 9,439,625, 9,575,165, 9,639,056, and 20080287783.

Any suitable disclosure above can be incorporated into any of the embodiments below. For example, aspects of devices, systems, and methods of manufacture and use are incorporated herein and can be incorporated into any of the embodiments below unless specifically indicated to the contrary.

Figures 8A, 8B:
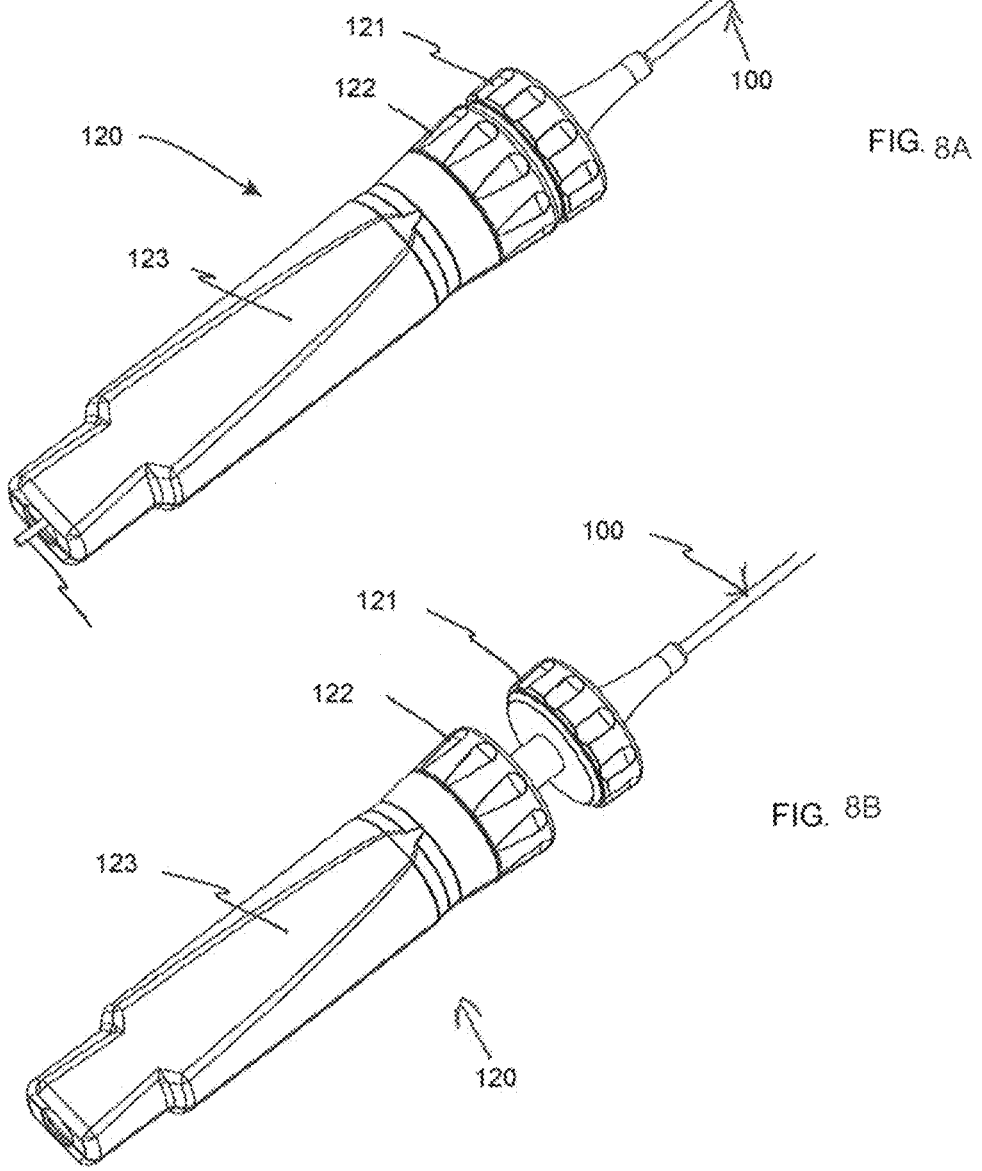
FIGS. 8A and 8B illustrate an exemplary handle assembly that can be used with any of the inner and outer elongate bodies or shafts herein.

FIGS. 8A and 8B illustrate a merely exemplary handle assembly that may be in operable communication with outer shaft 131 and inner shaft 132. In this exemplary implementation, handle assembly 120 includes handle body 123 that has an outer surface that can be gripped by a user, first actuator 121, and second actuator 122. Actuator 121 can be in operable communication with outer shaft 131, and actuator 122 can be in operable communication with inner shaft 132. Actuator 121 is adapted to be both rotated and moved axially relative to handle body 123 (and relative to second actuator 122). This allows actuator 121 to cause axial movement of the medical tool 103 and rotation of the medical tool 103 relative to a distal end of inner shaft 132. Second actuator 122 is adapted to be actuated (e.g., rotated in this embodiment) relative to handle body 123 to cause deflection of the inner shaft 132. For example, the handle assembly can have internal components that interface with proximal ends of pull wires such that actuation of actuator 122 tensions one or more pull wires to cause deflection of the inner shaft. In this embodiment actuator 121 is distal to actuator 122, but in other designs their relative positions could be reversed. FIG. 8B shows handle assembly 120 after actuator 121 has been advanced distally relative to its position in FIG. 8A. This distal advancement causes outer shaft 131 to be advanced distally, and thus causes the medical tool to be advanced distally. Actuator 121 can similarly be retracted proximally relative to its position in FIG. 8B. Tensioning members described further below are referenced with respect to actuator 121 being retracted proximally.

In other designs, actuator 121 could be in operable communication with an inner shaft and actuator 122 may be in operable communication with an outer shaft.

As described herein, the outer shaft can be moved axially relative to the inner deflectable shaft. The outer shaft may be constructed with sections of materials that vary in stiffness (e.g., durometer) along the length of at least a portion of the outer shaft. For example, a first portion that is distal to a second portion can have a lower durometer than the second portion. Because the outer shaft can be moved axially relative to the deflectable inner shaft, and because the stiffness of the outer shaft can vary along its length, the deflection, including the degree (or amount), of the overall device can be selectively controlled by controlling the axial position of the outer shaft (relative to the inner shaft). Axial movement of the outer shaft can thus selectively control deflection of the device. For example, a user (e.g., physician) can change or control where the bend occurs along the length of the device (measured from the distal end) by axially moving the outer shaft relative to the inner shaft. Additionally, for example, sections of varying stiffness in the outer shaft can allow for more or less deflection depending on the relative position of the outer shaft relative to the deflectable inner shaft. For example, deflecting the inner shaft at a region where the outer shaft has a relatively higher stiffness can result in less deflection than when the inner shaft is deflected at a region where the outer shaft has less stiffness.

FIG. 9C shows exemplary apparatus medical apparatus 130, which includes elongate inner shaft 132 (see FIG. 9A) and elongate outer shaft 131 (see FIG. 9B). Medical apparatus 130 may also be referred to herein as a "catheter," or other medical device that includes at least one elongate shaft.

FIG. 9D illustrates Section A-A shown in the assembly in FIG. 9C, which is a section in the deflectable section of the device. Parts from FIGS. 9A-9C are similarly labeled. As can be seen in FIG. 9D, pull wires 111 and 112 are very near to one another and about 180 degrees away from straightening pull wire 116.

As is also shown in FIG. 9D, elongate inner shaft 132 includes two layers of braided material 119, and the pull wires are, at least at the location of this section, essentially sandwiched between the two layers of braided material. Annular spaces 118 allow freedom of movement and space for optional lubricant. Inner shaft 132 may be made from, for example without limitation, a polymeric material such as Pebax, optionally with a lubricious additive. Inner shaft 132 may include liner 125, such as a PTFE liner. The flexible cable bundle 105 may be surrounded by one or more layers of insulation 126, such as PTFE insulation. Outer shaft 131 may comprise a polymeric material 127, such as Pebax. Outer shaft 131 may also include a radially inner liner 128, such as a PTFE liner. Any of the pullwires (e.g., 111, 112, 116) may be disposed in a lumen with a liner, such as PTFE liner 129.

Medical apparatus 130 (or either of elongate shaft 132 and elongate shaft 131, individually) can be in operable communication with any of the handle assemblies herein, including handle assembly 120 shown in FIGS. 8A and 8B.

FIGS. 10A-10C and FIG. 11 illustrate an additional exemplary handle assembly that can be in operable communication with any of the medical devices, including ultrasound probes, herein. For example, the exemplary handle assembly shown in FIGS. 10A-10C can be coupled to (directly or indirectly) and in operable communication with medical apparatus 130 shown in FIGS. 9A-9D. In a particular embodiment, both elongate outer shaft 131 and elongate inner shaft 132 are coupled to and in operable communication with the handle assembly shown in FIGS. 10A-10C.

The handle assembly in FIGS. 10A-10C and FIG. 11 has some similarities to the handle assemblies, the individual components, and subassemblies that are shown in FIGS. 8A and 8BB. Unless indicated to the contrary, concepts, features and methods of use from FIGS. 8A and 8B that can be incorporated into the handle assembly in FIGS. 10A-C are hereby incorporated by reference for all purposes into the disclosure of the handle assembly shown in, and described with respect to, FIGS. 10A-C. Similarly, concepts, features and methods of use that are shown in, and described with respect to, FIGS. 10A-C that can be incorporated into other handle assemblies herein are hereby incorporated by reference for all purposes into the disclosure of any of the handle assemblies set forth herein.

FIG. 10A is side view of handle assembly 140 with a portion of handle body 141 removed so that some internal components of the handle assembly can be seen. Handle assembly 140 includes first actuator 143 and second actuator 142, and in this embodiment first actuator 143 is distal to second actuator 142. First actuator 143 can be both moved axially and rotated relative to the handle body and relative to a second actuator (in this embodiment actuator 142). First actuator 143 is in operable communication with an outer elongate body, such as outer shaft 131 (see FIG. 9B). Axial movement of actuator 143 (distally or proximally) causes axial movement of the outer shaft 131, while rotation of actuator 143 causes rotation of the outer shaft. Second actuator 142 is in operable communication with an inner shaft, such as inner shaft 132 (FIG. 9A). Actuation of second actuator 142, in this embodiment rotation, causes deflection of the inner shaft. In this embodiment a rotatable and axially movable actuator (i.e., first actuator 143) is in operable communication with an outer shaft.

First actuator 143 is coupled to elongate outer shaft movement assembly 150 shown in the exploded view in FIG. 10B, such that movement of first actuator 143 causes movement of assembly 150. Elongate outer shaft movement assembly 150 is similarly coupled to the elongate outer shaft so that movement of first actuator also causes movement of the elongate outer shaft. In this embodiment, the outer elongate shaft is attached to removable part 153 after it is inserted into channel 156. Removable part 153 and channel 156 are configured so that removable part 153 is constrained by at least one inner surface of channel 156 when it is inserted therein. Elongate outer shaft movement assembly 150 also includes a distal head portion 151 that is secured to first actuator. Elongate outer shaft movement assembly 150 also includes a rotation limiting mechanism similar to that which is described herein, which limits the rotation of first actuator 143, and thereby limits the rotation of the outer elongate shaft. Any of the disclosure above related to rotation limiting subassemblies, functionality, and use, is incorporated into this embodiment for all purposes and may be incorporated into this and similar designs. During rotation, part 157 (see FIG. 10B) interacts with part 161, and part 162 interacts with part 158. The physical interactions of these two sets of parts limits rotation to the desired rotation limit, e.g., such as limiting rotation up to 630 degrees of rotation of the outer body (in other embodiments the allowed rotation could be more than 630 degrees, such as up to and including 720 degrees).

If it is desired to clean the outer shaft, for example after use, removable part 153 can be detached from the outer shaft to allow the outer shaft to be removed from the handle assembly and cleaned, before being reinserted and reattached to removable part 153 or a new removable part if part 153 is damaged or broken.

Handle assembly 140 also includes inner shaft deflection assembly 146, which is in operable communication with second actuator 142. Inner shaft deflection assembly 146 includes central gear 147 adapted and configured to rotate when second actuator 142 is rotated. Central gear 147 interfaces first spindle 148 and second spindle 149 via a geared interface, such that rotation of central gear 147 causes rotation of the spindles in the opposite direction. The inner shaft deflection assembly 146, including the spindles, extends further proximally than the elongate outer body movement assembly 150. The inner shaft extends through the outer shaft and extends further proximally than the outer shaft within handle assembly 150. This allows one or more pullwires that are part of the inner shaft to extend radially outward and interface with reels 160.

The lack of interaction between elongate outer shaft movement assembly 150 and elongate inner shaft movement assembly 146 allows for the inner and outer elongate shaft to be independently controlled by first actuator 143 and second actuator 142.

Handle assembly 140 also includes printed circuit board ("PCB") 170 disposed within handle body 141, the PCB being in electrical communication with a cable bundle, such as flexible cable bundle 105 in FIG. 53, or any of the cable bundles herein that are in communication with the medical tool, such as an ultrasound transducer.

Handle assembly 140 also includes a rotation indicator 180 that can be used to show a user the extent to which at least one of the first actuator and the second actuator are rotated relative to a home, or neutral position. First actuator 143 can include a rotation indicator 181 that is aligned along an axis with rotation indicator 180 when first actuator 143 is in a neutral position, as shown in FIG. 11. When first actuator 143 is rotated, rotation indicator 181 is rotated relative to the axis along which rotation indicator 180 extends, which enables the user to visually understand that first actuator 143, and thus the outer shaft, is rotated to some extent relative to the neutral position. Similarly, second actuator 142 can also have rotation indicator 182 that is aligned along an axis with rotation indicator 180 when second actuator 142 is in a neutral position, as shown in FIG. 11. When second actuator 143 is rotated, rotation indicator 182 is rotated relative to the axis along which rotation indicator 180 extends, which enables the user to visually understand that second actuator 143, and thus the inner shaft, is deflected to some extent relative to its neutral position.

In some alternative embodiments, the handle assembly can include one or more sensors to track how much rotation has occurred for the outer shaft, or how much deflection has occurred in the inner shaft. In some embodiments the handle assembly can include an encoder for each actuator.

In any of the embodiments herein that include an outer shaft and an inner shaft, the device can include one or more lubricants between the inner and outer shafts to make it easier to move the inner and outer shafts relative to one another by reducing friction between the two. If the medical device needs to be cleaned for reuse, additional lubricant can be added between the inner and outer shafts after the cleaning process.

In some embodiments herein the medical device may include a flexible member, such as a flexible conductor bundle (which may be referred to herein as a conductor bundle, flex bundle or other similar derivative thereof), coupled to and extending from a distal region (e.g., probe tip) towards a proximal region of the medical device (see, for example, conductor bundle 2020 shown in exemplary FIGS. 4-6G; or bundle 105 from FIG. 9B). A probe tip may include an ultrasound transducer in electrical communication with a flexible conductor bundle. In some embodiments herein (e.g., FIGS. 9A-11), the probe tip and conductor bundle can be axially displaced (proximally and/or distally) by actuation of a handle actuator (e.g., actuator 143 as shown in FIG. 10A). In some instances, the conductor bundle is disposed within an elongate member (e.g., steerable inner elongate body 132; or elongate member 131) and moves axially relative thereto when the probe tip is advanced distally or retracted proximally. When the distal region (e.g., ultrasound probe) and conductor bundle are retracted proximally (after being advanced distally), the conductor bundle may tend to fold up, bunch up, or otherwise bend, near or adjacent to its distal end due to friction between the bundle and, for example, the elongate member (e.g., steerable inner shaft 132) in which the conductor bundle is disposed. Bunching may occur if the medical device is in a straight configuration as well as if the medical device has some degree of bend (e.g., after being deflected from a straight or linear configuration).

To reduce the degree of, or even prevent completely, a tendency to bunch up or bend, any of the medical devices herein may include a structural tensioning member that is adapted and configured to apply or maintain tension on the flexible member, such as a flexible conductor bundle, at a location that is proximal to where the conductor bundle is coupled to the distal medical tool. By tensioning the flexible member, folding or bunching up of the flexible member can be minimized or even prevented. When used in this context, the "tensioning" member is adapted and configured to reduce distal region(s) of the flexible conductor from bunching (compared to a device without a tensioning member) by proximally moving at least a distal portion of the flexible conductor bundle as the distal probe is retracted proximally. In some embodiments, the structural tensioning member (e.g., a tensioning bar) may be physically secured to the flexible conductor bundle (e.g., direct or indirect attachment). In general, the tensioning members herein are in operable communication with the flexible members (e.g., a flex conductor bundle) such that movement or actuation of the tensioning member applies some force to the flexible member, and may cause movement (e.g., proximal) of the flexible member. In some exemplary embodiments the structural tensioning member may be disposed in or carried by the handle assembly of the medical device. Structural tensioning member in this context may be a single component or an assembly of separate components.

FIGS. 12A-12F illustrate a handle assembly portion of an exemplary medical device, which may be incorporated into any suitable medical device herein. For example, the handle assembly in FIGS. 12A-12F may be part of a medical device that includes a medical tool (e.g., an ultrasound imaging probe) at its distal end or near its distal end, examples of which are described herein. Any other embodiment or feature herein is incorporated by reference into the exemplary handle assembly shown in FIGS. 12A-12F.

Exemplary handle assembly 310 includes first actuator 314 and second actuator 322, where first actuator 314 is distal to proximal actuator 322. First actuator 314 is adapted and configured to be moved axially (distally and proximally) relative to second actuator 322 (and optionally also rotatable relative thereto), and may be in operable communication with an elongate body (e.g., 131 or 132) that may include a medical tool (e.g., 103) in a distal region. Handle assembly 310 (including actuators) may incorporate any of the relevant disclosure from any other handle assembly herein. The medical device of which handle assembly 310 is a part also includes a flexible member (e.g., flexible conductor bundle 105 in FIG. 9B) securely coupled to (directly or indirectly) the medical tool at a first distal location (e.g., as shown in FIGS. 9B and 9C where medical tool 103 is secured to flexible member 105) and extends proximally from the medical tool towards handle assembly 310. The flexible member may be a flexible conductor bundle and can extend into handle assembly 310, as shown. A portion of the flexible member is disposed within an outer surface of the elongate body (e.g., within 131 and/or 132). The medical device also includes tensioning member that is secured to the flexible member at a second location 316, which is proximal to the first location ("first location" in this context may be referred to as a first distal location or derivative thereof). FIG. 12A illustrates exemplary tensioning member 312, while reference number 312 in FIG. 12A also points to an optional elongate rigid member (in this embodiment the elongate rigid member is linear and extending axially) of the tensioning member. Tensioning member 312 is adapted and configured to tension the flexible member as the medical tool is retracted proximally. This may be referred herein as applying a tensile force to the flexible member, or tensioning the flexible member, or maintaining tension in the flexible member. In this exemplary embodiment, tensioning member 312 is adapted and configured to tension the flexible member as the medical tool is retracted proximally, which in this embodiment occurs when first actuator 314 is retracted proximally from its position shown in FIG. 12A-C. The tensioning members herein can apply tension when the medical device is in a straight configuration and when the medical device is in a non-straight (linear) configuration, such as when the device may be deflected or bent.

In this embodiment, tensioning member 312 (which may include the tensioning bar shown in FIG. 12A) is secured to (e.g., attached directly) the flexible conductor bundle at location 316, the location of which is inside the handle assembly in this embodiment. In another embodiment, the tensioning member 312 may be secured to the flexible conductor bundle at an alternate location 317. A tensioning member may alternatively be secured to the flexible member at a location that is inside a handle or outside of the handle, such as inside one or both of outer and inner shafts. In this embodiment the tensioning member is also axially secured relative to first actuator 314, such that axial movement of first actuator 314 causes axial movement of tensioning member 312 (which may be in a 1:1 movement ratio). Because tensioning member 312 is also secured to the flexible member (e.g., at location 316), axially movement of tensioning member 312 also causes axial movement of the flexible member at location 316. By securing tensioning member 312 to the flexible member, the flexible member is tensioned distal to where the tensioning member is secured to the flexible member when first actuator 314 is retracted proximally, which prevents the flexible member from folding or bunching up at its distal region near or adjacent to the medical tool (or at least reduces the extent of folding/bunching up compared to a device without a tensioning member).

The flexible member may include a flexible conductor bundle, such as any of the flexible conductor bundles herein. In FIGS. 12A-F, the tensioning member comprises a rigid elongate member (generally referred to as 312 in FIG. 12A) with a fixed length. The rigid tensioning member as shown has a general longitudinal axis, which in this embodiment is parallel with a longitudinal axis of the medical device and/or a longitudinal axis of the handle assembly. The rigid tensioning member may be made of a variety of materials, such as a rigid plastic member.

The tensioning members herein can ensure that the distance traveled by the medical tool is the same as the distance traveled by any point on the flexible member between the first and second locations. The tensioning members herein can ensure that the distance traveled by the medical tool is the same as the distance traveled by the location where the tensioning member is secured to the flexible member (e.g., location 316 in FIG. 12A).

The secured relationship between the tensioning member and the flexible member maintains the flexible member in a substantially flat or straight configuration between the first and second locations as the medical tool is retracted proximally (when the medical device is a straight configuration). A flat configuration in this context can include embodiments in which the flexible member may also be twisted (i.e., the flexible member can be flat and still be twisted, but not bunched/folded). A flattened configuration as used herein indicates a lack of a fold or bunching of the flexible member.

Medical devices in which a tensioning member is incorporated may also be steerable or deflectable. The tensioning members herein can be adapted and configured to apply a tensile force to the flexible member even if the medical device, including the flexible member, are in non-straight (e.g., deflected, steered, bent) configurations. When this disclosure refers to maintaining a substantially flat configuration in the flexible member, it refers to instances where the medical device may be in a straight configuration, which need not be the case, such as when a medical device has been steered, bent, or deflected.

The secured relationship between the tensioning members and the flexible members herein prevents the flexible member from forming a fold (i.e., bending, or bunching up) between the first and second locations as the medical tool is retracted proximally. Folding, bending, and bunching-up in this context includes a first region of the flexible member axially overlapping with a second region of the flexible member, and also includes general bending and bunching of the flexible member, such as regions of the flexible member that are not flat and, for example, form a bend, curved region, and/or meander back and forth.

The flexible member may have flat top and bottom surfaces (e.g., a conductor bundle with one or more flat surfaces), and optionally the tensioning member may be secured to at least one of the top and bottom surfaces. For example, FIGS. 6A-6G illustrate a flexible member with flat or generally flat first and second surface (e.g., top and bottom surfaces), and a tensioning member may be secured to one or both of the flat or generally flat surfaces (e.g., such as at location 316). They may be secured using a variety of techniques, such as using adhesive, welding, or other bonding techniques.

The tensioning member may be in operative communication (directly or indirectly) with a handle actuator such that axial movement of the actuator axially moves the tensioning member. The handle actuator may be further adapted and configured to be rotated (e.g., actuator 314) to cause rotation of the medical tool, and optionally wherein rotation of the actuator does not cause rotation of the tensioning member. The tensioning member can thus be adapted to be moved axially when the actuator is moved axially, but not to rotate when the actuator is rotated. This can be accomplished by the manner in which the tensioning member is operatively in communication (directly or indirectly) with the actuator.

The medical device may include an inner elongate body (e.g., 132) including a lumen in which at least a portion of the flexible member is disposed. An inner elongate body may be independently steerable, such as with a separate independently actuatable handle actuator (e.g., actuator 322). Aspects of other embodiments herein in which the medical device includes an inner member and outer member, the inner member independently controllable (e.g., axially and rotationally) are fully incorporated in any of the embodiments herein.

The flexible member may be coupled to a printed circuit board (e.g., 321 "boards" as shown in FIG. 12A) in the handle assembly. The tensioning member may be coupled to a flexible member proximal to a printed circuit board. In alternative embodiments the tensioning member may be coupled to a flexible member distal to a printed circuit board.

FIGS. 12A-12F is an example of a portion of a medical device that includes an elongate outer body (e.g., 131) including a probe tip in a distal region of the elongate body; a flexible conductor bundle (e.g., 105) securely coupled to the probe tip at a first location (shown in figure FIGS. 9B and 9C) and extending proximally from the medical tool and into a handle assembly, the flexible member disposed within an outer surface of the elongate body; an inner elongate body (e.g., 131), at least a portion of which is disposed within the elongate outer body, the inner elongate body optionally steerable, wherein at least a portion of the flexible conductor bundle is disposed within the inner elongate body and configured to be axially movable relative to the inner elongate body; a tensioning member secured to the flexible member at a second location in the handle assembly, the tensioning member adapted and configured to apply tension on the flexible member as the probe tip is retracted proximally. Probe tips as used herein may include one or more ultrasound transducers.

FIGS. 12E-F illustrate a half of a handle outer shell 320, two of which form a portion of the outer surfaces of the handle assembly 310. Handle shells 320 include radially inwardly extending features 315 that are adapted to interface with a control the movement of the tensioning member 312. Features 315 can include guides that are configured to interface with the tensioning member at one or more locations and help stabilize the tensioning member.

Any other handle assembly component in any other embodiment herein that can be suitably integrated into handle assembly 310 is incorporated by reference herein.

In any of the embodiments and claims herein, the phrase "tensioning member" may be replaced with "straightening member," "flattening member," or a derivative thereof. As described herein, a straightening member or flattening member refers to maintaining a substantially straight or flattened configuration in the flexible member when the medical device is in a straightened configuration, and does not require that the device always has a straightened configuration. Thus, even if the flexible member is not necessarily being placed under tension, it may still be maintained in a straightened (i.e., not folded configuration) along at least a portion of its length due to a straightening member. Member 312 in FIG. 12A, for example, is an example of a straightening member, even if it also functions as a tensioning member. This applies to all tensioning members described, shown, and claimed herein. In some embodiments herein, the "member" can be a straightening member (or flattening member) and can also function as a tensioning member. Additionally, the phrase "tensioning member" herein may be replaced with "fold-prevention member," "bend-prevention member," "bunching-prevention member," or a derivative thereof.

The disclosure above describes that in some embodiments the flexible member, such as conductor bundle 2010, may be twisted along a portion of its length. For example, a conductor bundle may be twisted to provide a more balanced cross-section along a portion of the length of the medical device. A conductor bundle may be twisted only in a portion of the medical device that will experience deflection.

FIGS. 13A-13E illustrate a portion of an exemplary medical device that includes a twisted flexible member, such as a flexible conductor bundle. The embodiment in FIGS. 13A-E may be incorporated with any other suitable feature and/or medical device described herein.

The portion 330 of the medical device shown in FIGS. 13A-E includes a medical tool 332 at a distal region, a flexible member 331 coupled thereto and extending proximally therefrom, and a proximal end region 333 comprising a plurality of electrical connectors. Flexible member 331 may be a flexible conductor bundle, such as any of the bundles herein. Medical tool 332 may include an ultrasound imaging transducer 339. Flexible conductor bundle 331 has a region 338 in which the conductor bundle is twisted, the twisted region 338 having a distal end and a proximal end. Flexible conductor bundle 331 also includes a region 336 distal to twisted region 334 that is not twisted, and a region 340 proximal to twisted region 336 that is not twisted. Medical tool 332 may be coupled to an outer shaft, such as outer shaft 131 shown in FIG. 9B.

The length of twisted region 338 from its distal end to its proximal end can vary, and in some embodiments is from 5-15 cm, such as from 8-15 cm, such as 11 cm. The length over which a complete turn is formed can vary well, such as from 1-5 cm, such as 3 cm.

The number of twists over the length of the twisted region can vary as well, such as, for example without limitation, 7-9 full twists.

An exemplary manner in which to form the twisted region of the flexible member (e.g., flexible conductor bundle) is to couple the flexible member to the medical tool at the distal end (e.g., probe tip). A thin section of PET heat shrink may then be advanced over the flexible conductor bundle. A portion of the device can be held in place while another portion is twisted to the desired number of turns to form the twisted region. While the twisted configuration is maintained, the PET can be heat shrunk over the twisted bundle region. Additional layers of PET may be subsequently added. An elongate member (e.g., shaft 131) may then be placed over the bundle, including the twisted region, and the elongate member can be bonded to the medical tool.

The invention claimed is:

1. A medical device configured and sized to be positioned within a subject, comprising:

an ultrasound transducer in a distal region of the medical device, the ultrasound transducer secured to an outer shaft;

a flexible conductor bundle secured to the ultrasound transducer at a first location in the distal region, the flexible conductor bundle extending proximally from the first location and into a handle assembly of the medical device, the flexible conductor bundle extending within the outer shaft of the medical device and within an inner shaft of the medical device, the flexible conductor bundle movable within the inner shaft; at least a portion of the inner shaft disposed within the outer shaft; and a tensioning member directly secured to one or more surfaces of the flexible conductor bundle at a second location within the handle assembly, the tensioning member and the ultrasound transducer in operable communication with a handle actuator such that actuation of the handle actuator causes movement of the ultrasound transducer and the tensioning member, to thereby apply tension to the flexible conductor bundle at the second location within the handle assembly.

2. A medical device of claim 1, wherein the inner shaft is in operable communication with a second handle actuator such that the inner shaft is deflectable upon actuation of the second handle actuator.

3. A medical device of claim 1, wherein the tensioning member is secured to the flexible conductor bundle at the second location such that the tensioning member and flexible conductor bundle move together at the second location upon actuation of the handle actuator.

4. A medical device of claim 1, wherein the tensioning member is secured to the flexible conductor bundle such that the flexible conductor bundle is maintained in a substantially flattened configuration between the first and second locations when the ultrasound transducer is retracted proximally.

5. A medical device of claim 4, wherein the tensioning member is secured to the flexible conductor bundle to prevent the flexible conductor bundle from folding between the first and second locations as the ultrasound transducer is retracted proximally.

6. A medical device of claim 1, wherein the flexible conductor bundle has flat or generally flat first and second surfaces, and wherein the tensioning member is secured to one or both of the flat or generally flat first and second surfaces.

7. A medical device of claim 1, wherein the handle actuator is also adapted to be rotated to cause rotation of the ultrasound transducer, and wherein the tensioning member and the actuator are in operative communication such that rotation of the handle actuator does not cause rotation of the tensioning member.

8. A medical device of claim 1, wherein the flexible conductor bundle is coupled to a printed circuit board in the handle assembly.

9. A medical device of claim 8, wherein the second location is proximal to the printed circuit board.

10. A medical device configured and sized to be positioned within a subject, comprising:

an ultrasound transducer in a distal region of the medical device, the ultrasound transducer secured to an outer shaft;

a flexible conductor bundle secured to the ultrasound transducer at a first location in the distal region, the flexible conductor bundle extending proximally from the first location and into a handle assembly of the medical device, the flexible conductor bundle extending within the outer elongate shaft of the medical device and within an inner shaft of the medical device, the flexible conductor bundle movable within the inner shaft; at least a portion of the inner shaft disposed within the outer shaft; and a flexible conductor flattening member directly secured to one or more surfaces of the flexible conductor bundle at a second location within the handle assembly, the flexible conductor flattening member and the ultrasound transducer tip in operable communication with a handle actuator such that actuation of the handle actuator causes movement of the ultrasound transducer and the flexible conductor flattening member, to thereby maintain the flexible conductor bundle in a flattened configuration between the first and second locations.

11. A medical device configured and sized to be positioned within a subject, comprising:

an ultrasound transducer in a distal region of the medical device, the ultrasound transducer secured to an outer shaft;

a flexible conductor bundle secured to the ultrasound transducer at a first location in the distal region, the flexible conductor bundle extending proximally from the first location and into a handle assembly of the medical device, the flexible conductor bundle extending within the outer shaft of the medical device and within an inner shaft of the medical device, the flexible conductor bundle movable within the inner shaft; at least a portion of the inner shaft disposed within the outer shaft; and a flexible conductor bend prevention member directly secured to one or more surfaces of the flexible conductor bundle at a second location within the handle assembly, the flexible conductor bend prevention member and the ultrasound transducer tip in operable communication with a handle actuator such that actuation of the handle actuator causes movement of the ultrasound transducer and the flexible conductor bend prevention member, to thereby prevent the flexible conductor bundle from bending between the first and second locations.

12. A method of using a medical device that is configured and sized to be positioned within a subject, the medical device comprising:

an ultrasound transducer in a distal region of the medical device, the ultrasound transducer secured to an outer shaft;

a flexible conductor bundle secured to the ultrasound transducer at a first location in the distal region, the flexible conductor bundle extending proximally from the first location and into a handle assembly of the medical device, the flexible conductor bundle extending within the outer shaft of the medical device and within an inner shaft of the medical device, the flexible conductor bundle movable within the inner shaft; at least a portion of the inner shaft disposed within the outer shaft; and a tensioning member directly secured to one or more surfaces of the flexible conductor bundle at a second location within the handle assembly, the tensioning member and the ultrasound transducer in operable communication with a handle actuator such that actuation of the handle actuator causes movement of the ultrasound transducer and the tensioning member, to thereby apply tension to the flexible conductor bundle at the second location within the handle assembly; the method comprising:

positioning the ultrasound transducer within the subject;

proximally retracting the ultrasound transducer; and applying tension to the flexible conductor bundle at the second location within the handle assembly while proximally retracting the ultrasound transducer.

13. The method of claim 12, further comprising actuating the handle actuator, wherein actuating the handle actuator causes the proximal retraction of the ultrasound transducer and causes the application of tension to the flexible conductor bundle at the second location within the handle assembly.

14. The method of claim 12, wherein applying tension to the flexible conductor bundle prevents folding in the flexible conductor bundle distal to the second location within the handle assembly.

15. The method of claim 12, wherein applying tension to the flexible conductor bundle comprises moving the tensioning member proximally within the handle assembly.

16. The method of claim 15, the method further comprising actuating the handle actuator to cause the proximal movement of the tensioning member and the application of tension to the flexible conductor bundle.

17. The method of claim 16, wherein actuating the handle actuator causes the proximal retraction of the ultrasound transducer.

18. A method of using a medical device that is configured and sized to be positioned within a subject, the medical device comprising:

an ultrasound transducer in a distal region of the medical device, the ultrasound transducer secured to an outer shaft;

a flexible conductor bundle secured to the ultrasound transducer at a first location in the distal region, the flexible conductor bundle extending proximally from the first location and into a handle assembly of the medical device, the flexible conductor bundle extending within the outer shaft of the medical device and within an inner shaft of the medical device, the flexible conductor bundle movable within the inner shaft; at least a portion of the inner shaft disposed within the outer shaft; and a tensioning member directly secured to one or more surfaces of the flexible conductor bundle at a second location within the handle assembly, the tensioning member and the ultrasound transducer in operable communication with a handle actuator such that actuation of the handle actuator causes movement of the ultrasound transducer and the tensioning member, to thereby apply tension to the flexible conductor bundle at the second location within the handle assembly; the method comprising:

positioning the ultrasound transducer within the subject;

proximally retracting the ultrasound transducer; and applying a force to the flexible conductor bundle at the second location within the handle assembly while proximally retracting the ultrasound transducer.

19. The method of claim 18, wherein applying the force to the flexible conductor bundle at the second location maintains the flexible conductor bundle in a flattened configuration between the first and second locations.

* * * * *